US011001562B2

(12) United States Patent
Frangioni et al.

(10) Patent No.: US 11,001,562 B2
(45) Date of Patent: May 11, 2021

(54) NEAR-INFRARED FLUORESCENT NERVE CONTRAST AGENTS AND METHODS OF USE THEREOF

(71) Applicants: Beth Israel Deaconess Medical Center, Boston, MA (US); Georgia State University Research Foundation Inc., Atlanta, GA (US)

(72) Inventors: John V. Frangioni, Wayland, MA (US); Hak Soo Choi, Needham, MA (US); Maged M. Henary, Atlanta, GA (US)

(73) Assignees: Beth Israel Deaconess Medical Center, Boston, MA (US); Georgia State University Research Foundation Inc., Atlanta, GA (US)

(*) Notice: Subject to any disclaimer, the term of this patent is extended or adjusted under 35 U.S.C. 154(b) by 644 days.

(21) Appl. No.: 15/033,322

(22) PCT Filed: Oct. 30, 2014

(86) PCT No.: PCT/US2014/063104
§ 371 (c)(1),
(2) Date: Apr. 29, 2016

(87) PCT Pub. No.: WO2015/066296
PCT Pub. Date: May 7, 2015

(65) Prior Publication Data
US 2016/0347727 A1    Dec. 1, 2016

Related U.S. Application Data

(60) Provisional application No. 61/898,424, filed on Oct. 31, 2013.

(51) Int. Cl.
| | | |
|---|---|---|
| *A61K 51/00* | (2006.01) | |
| *A61M 36/14* | (2006.01) | |
| *C07D 265/38* | (2006.01) | |
| *C07D 498/14* | (2006.01) | |
| *A61K 49/00* | (2006.01) | |
| *A61K 51/04* | (2006.01) | |
| *C07D 265/34* | (2006.01) | |

(52) U.S. Cl.
CPC .......... *C07D 265/38* (2013.01); *A61K 49/003* (2013.01); *A61K 49/0026* (2013.01); *A61K 49/0028* (2013.01); *A61K 49/0052* (2013.01); *A61K 51/0463* (2013.01); *C07D 265/34* (2013.01); *C07D 498/14* (2013.01); *A61K 49/0017* (2013.01)

(58) Field of Classification Search
None
See application file for complete search history.

(56) References Cited

U.S. PATENT DOCUMENTS

| 6,083,485 A | 7/2000 | Licha et al. |
|---|---|---|
| 6,258,340 B1 | 7/2001 | Licha et al. |
| 6,440,389 B1 * | 8/2002 | Rabito ............... A61K 49/0028 424/9.6 |
| 6,913,743 B2 | 7/2005 | Licha et al. |
| 6,926,885 B2 | 8/2005 | Licha et al. |
| 7,025,949 B2 | 4/2006 | Licha et al. |
| 7,445,767 B2 | 11/2008 | Licha et al. |
| 7,582,483 B2 | 9/2009 | Mizutani et al. |
| 7,655,217 B2 | 2/2010 | Licha et al. |
| 7,682,603 B2 * | 3/2010 | Hammer ............ A61K 49/0021 424/9.61 |
| 8,173,819 B2 | 5/2012 | Rajopadhye et al. |
| 8,268,014 B2 | 9/2012 | Frohling |
| 8,460,639 B2 | 6/2013 | Nomoto et al. |
| 2001/0055567 A1 | 12/2001 | Licha et al. |
| 2003/0026762 A1 | 2/2003 | Malmros et al. |
| 2003/0026763 A1 | 2/2003 | Licha et al. |
| 2003/0170179 A1 | 9/2003 | Licha et al. |
| 2004/0028611 A1 | 2/2004 | Frangioni |
| 2004/0029837 A1 | 2/2004 | Fries et al. |
| 2004/0062713 A1 | 4/2004 | Matsuo et al. |
| 2005/0106106 A1 | 5/2005 | Licha et al. |
| 2005/0169844 A1 | 8/2005 | Licha et al. |
| 2006/0040400 A1 | 2/2006 | Mizutani et al. |
| 2006/0165598 A1 | 7/2006 | Licha et al. |
| 2006/0165599 A1 | 7/2006 | Licha et al. |
| 2006/0275209 A1 | 12/2006 | Schweiger et al. |
| 2007/0292883 A1 | 12/2007 | Ossovskaya et al. |
| 2008/0308744 A1 | 12/2008 | Frangioni et al. |
| 2008/0318336 A1 | 12/2008 | Scherninski et al. |
| 2009/0269277 A1 * | 10/2009 | Chang .............. A61K 47/48746 424/1.49 |

(Continued)

FOREIGN PATENT DOCUMENTS

| JP | H5-150395 A | 6/1993 |
|---|---|---|
| JP | 2000-95758 A | 4/2000 |

(Continued)

OTHER PUBLICATIONS

Abugo et al. (Analyt. Biochem. 2000, 279, 142-150).*
Ghanadzadeh et al. (Spectrochimica Acta Part A 2009, 73, 324-329).*
Dao et al. (Australas Phys Eng Sci Med 2004, 27, 224-229).*
Sloviter (Cancer Res. 1949, 9, 677-680).*
Ciba-Geigy AG, "Use of dyes for shading during optical brightening of polyester and polyacrylonitrile substrates", Research Disclosure, 1982, vol. 216, Article No. 21611, pp. 107-109.
Yuan, L. et al. "A unique class of near-infrared functional fluorescent dyes with carboxylic-acid-modulated fluorescence On/Off switching rational design, synthesis, optical properties, theoretical calculations, and applications for fluorescence imaging in living animals", Journal of the American Chemical Society, 2012, vol. 134, No. 2, pp. 1200-1211.

(Continued)

*Primary Examiner* — Michael G. Hartley
*Assistant Examiner* — Melissa J Perreira
(74) *Attorney, Agent, or Firm* — Locke Lord LLP; Nicholas J. DiCeglie, Jr.

(57) ABSTRACT

The instant invention provides near-infrared fluorescent nerve contrast agents and methods of using them.

5 Claims, 12 Drawing Sheets

(56) References Cited

U.S. PATENT DOCUMENTS

| | | | |
|---|---|---|---|
| 2010/0035871 A1* | 2/2010 | Stack | C07D 265/36 |
| | | | 514/230.5 |
| 2010/0129293 A1 | 5/2010 | Licha et al. | |
| 2010/0323389 A1 | 12/2010 | Xu et al. | |
| 2012/0017931 A1 | 1/2012 | Frohling | |
| 2012/0045851 A1 | 2/2012 | Scherninski et al. | |
| 2013/0030282 A1 | 1/2013 | Margel et al. | |
| 2014/0063097 A1 | 3/2014 | Liu et al. | |
| 2015/0209451 A1 | 7/2015 | Frangioni et al. | |
| 2017/0290927 A1 | 10/2017 | Frangioni et al. | |

FOREIGN PATENT DOCUMENTS

| | | |
|---|---|---|
| JP | 2005-524072 A | 8/2005 |
| JP | 2007-508282 A | 4/2007 |
| JP | 2009-507035 A | 2/2009 |
| JP | 2010-169677 A | 8/2010 |
| JP | 2011-503067 A | 1/2011 |
| JP | 2012-524153 A | 10/2012 |
| JP | 2013-523725 A | 6/2013 |
| JP | 2013-199477 A | 10/2013 |
| WO | 2005/082423 A2 | 9/2005 |
| WO | 2007/017602 A2 | 2/2007 |
| WO | 2009/061473 A2 | 5/2009 |
| WO | 2010/091243 A1 | 8/2010 |
| WO | 2010/121163 A2 | 10/2010 |
| WO | 2012/063028 A1 | 5/2012 |

OTHER PUBLICATIONS

James, N.S. et al., "Evaluation of polymethine dyes as potential probes for near infrared fluorescence imaging of tumors: Part 1", Theranostics, Aug. 2013, vol. 3, No. 9, pp. 692-702.

Quek, C.-H. et al. "Near-infrared fluorescent nanoprobes for in vivo optical imaging", Nanomaterials, 2012, vol. 2, No. 2, pp. 92-112.

Ashitate, Y., et al. "Simultaneous mapping of pan and sentinel lymph nodes for real-time image guided surgery", Theranostics, Apr. 2014, vol. 4, No. 7, pp. 693-700.

Amiot, C. L. et al., "Near-infrared fluorescent materials for sensing of biological targets", Sensors, 2008, vol. 8, No. 5, pp. 3082-3105.

Tibbe, A. G. J. et al., "Imaging technique implemented in CellTracks system," Cytometry, 2002, vol. 47, No. 4, pp. 248-255.

International Search Report issued in PCT/US2014/063104, dated Feb. 26, 2015.

International Search Report issued in PCT/US2014/063097, dated Apr. 10, 2015.

Chemical Physics Letters, Mar. 1996, vol. 250 pp. 261-265.

Gibbs "Near infrared fluorescence for image-guided surgery" Quant Imaging Med Surg, Jan. 1, 2012, pp. 177-187.

Journal of Photopolymer Science and Technology, 2000, vol. 13, No. 2, pp. 183-186.

Proceedings of SPIE, 2011, vol. 8114, pp. 81140 T-1 to 81140 T-9.

Sano, K. "Short PEG-linkers improve the performance of targeted, activatable monoclonal antibody-indocyanine green optical imaging probes" Bioconjugate Chemistry, 2013 24(5), pp. 811-816.

European Journal of Medicinal Chemistry, 2012, vol. 54, pp. 647-659.

Office Action issued in Japanese Patent Application No. JP 2016-552234, dated Oct. 21, 2020.

* cited by examiner

Chemical Structure of Nerve-Targeting Fluorophores. Oxazine 1 is also known as Oxazine 725.

*Ex Vivo* Screening Assay of Fluorophores for Nerve-Specificity.

Real-Time Intraoperative Fluorescence Images of RLN, BP and SN

Fluorescence Microscopic Images of Cryosectioned RLN, BP, and SN

BMB

LogD, pH 7.4 = 4.84

TPSA = 61.27 Å²

| | | | | |
|---|---|---|---|---|
| BMB | 1.000 | | BMB | 0.802 |
| Rhodamine 800 | 0.444 | | Oxazine 4 | 0.415 |
| Oxazine 4 | 0.418 | | Rhodamine 800 | 0.414 |
| Oxazine 170 | 0.415 | | Oxazine 170 | 0.411 |
| Oxazine 750 | 0.408 | | Oxazine 1 | 0.396 |
| Oxazine 1 | 0.400 | | Oxazine 750 | 0.391 |

Chemical Similarities Between Non-NIR and NIR Nerve-Specific Contrast Agents.

Optical Properties of Nerve-Targeting Fluorophores

Optical Properties of Oxazine 4 in Various Solvents

| Solvent | Extinction Coefficient ($M^{-1}cm^{-1}$) | Peak Absorbance (nm) | Peak Emission (nm) | Stokes Shift (nm) |
|---|---|---|---|---|
| PBS | 143,000 | 616 | 634 | 17 |
| FBS | 143,000 | 616 | 635 | 17 |
| MeOH | 182,000 | 611 | 631 | 20 |
| DMSO | 147,000 | 621 | 640 | 19 |

DMSO = dimethyl sulfoxide; FBS = bovine serum supplemented with 50 mM HEPES, pH 7.4; MeOH = mehanol; PBS = phosphate buffered saline, PH 7.4.

Optical Properties of Nerve-Targeting Fluorophores

Fig. 6B

*In Vivo* Screening Assay of Fluorophores for Nerve-Specificity

Chemical Similarity Calculated by Comparing Fluorophores to Positive Nerve Binding Fingerprints

NEAR-INFRARED FLUORESCENT NERVE CONTRAST AGENTS AND METHODS OF USE THEREOF

RELATED APPLICATIONS

This application is a 35 U.S.C. § 371 National Phase Application of International PCT Patent Application No. PCT/US2014/063104, filed Oct. 30, 2014 which application claims the benefit of priority to U.S. Provisional Patent Application No. 61/898,424 filed Oct. 31, 2013, the contents of which are incorporated herein by reference in their entirety.

GOVERNMENT SUPPORT

This invention was made with government support under CA115296, EB010022, and EB011523 awarded by NIH. The Government has certain rights in the invention.

BACKGROUND

Nerve damage during surgery results in significant morbidity and mortality (1-4). Despite advancements in surgical technique and equipment, nerves are currently identified via gross appearance and anatomical location, without intraoperative image guidance. Thin or buried nerves are at high risk for damage. Anatomical variants such as bifurcation, trifurcation, medial or anterior displacement, and non-recurrence are also risk factors for injury (5, 6). For example, recurrent laryngeal nerve (RLN) injury can cause symptoms ranging from hoarseness and aspiration in unilateral injury, to life threatening airway obstruction in the case of bilateral injury (2, 7). To minimize such high morbidity and mortality from nerve injury, intraoperative visual identification during complex surgery is of paramount importance.

However, only 3 main classes of nerve cell-specific molecules have been reported to date, including stilbene derivatives, distyrylbenzene (DSB) fluorophores, and styryl pyridinium (FM) fluorophores (8-11). Among these agents, DSBs such as GE3082 and GE3111 have been investigated for image-guided nerve surgery (12-14). However, none of these compounds were optimal because of high adsorption and scattering in tissues from the ultraviolet and visible wavelengths required. In addition, due to their intrinsically high lipophilicity and charge, they exhibit high background binding to adipose tissues, thus lowering the signal-to-background ratio (SBR) considerably. Relatively high endogenous tissue autofluorescence in the visible wavelength range also limits the use of these fluorophores in vivo (15).

To overcome these limitations, nerve-specific contrast agents in the near-infrared (NIR) range are desperately needed. Recently, Whitney et al. synthesized peptides that localize to nerve-associated connective tissues (16). They targeted almost all nerves in the body including motor and sensory nerves, but only after labeling with exogenous fluorophores (16, 17). Gibbs et al. investigated the structure-activity relationship (SAR) of over 200 nerve cell-specific contrast agents and also screened these molecules for NIR optical properties. Although no NIR agents were obtained, several putative fingerprints for nerve uptake were identified (13).

In view of the disadvantages of known contrast reagents, nerve-specific contrast agents in the near-infrared (NIR) range are needed.

SUMMARY

The present invention is directed, at least in part, to near-infrared fluorescent nerve contrast agents and methods of using them.

In one aspect, the invention provides a method of imaging tissue or cells, the method comprising:

(a) contacting the tissue or cells with an imaging agent represented by the formula (Formula I):

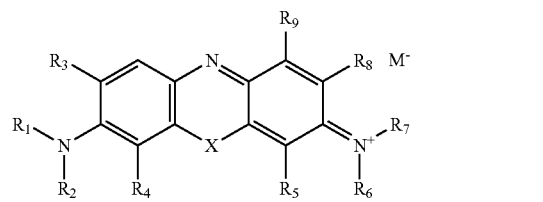

(Formula I)

in which $R_1$, $R_2$, $R_3$, $R_4$, $R_6$ and $R_7$ are each independently H or Y—$C_1$-$C_6$ alkyl, where Y is NH, S, Se, Si, B, or O;

$R_5$, $R_8$ and $R_9$ are each independently H, CN, OH, or $C_1$-$C_6$ alkyl;

or $R_1$ and $R_3$, taken together with the atoms to which they are connected, form a 5- to 7-membered heterocyclic ring;

or $R_2$ and $R_4$, taken together with the atoms to which they are connected, form a 5- to 7-membered heterocylic ring;

or $R_5$ and $R_6$, taken together with the atoms to which they are connected, form a 5- to 7-membered heterocyclic ring;

or $R_7$ and $R_8$, taken together with the atoms to which they are connected, form a 5- to 7-membered heterocyclic ring;

or $R_8$ and $R_9$, taken together with the atoms to which they are connected, form an aryl or heteroaryl ring;

X is O, S, Se, N—R; where R=H or $C_1$-$C_6$ alkyl;

$M^-$ is an anion;

(b) irradiating the tissue or cells at a wavelength absorbed by the imaging agent; and (c) detecting an optical signal from the irradiated tissue or cells, thereby imaging the tissue or cells.

In certain embodiments, the tissue or cells is nerve tissue or nerve cells.

In certain embodiments, X is O.

In certain embodiments, the compound is represented by Formula Ia:

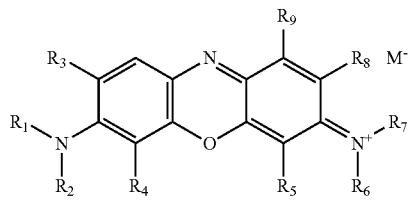

in which $R_1$, $R_2$, $R_3$, $R_4$, $R_6$ and $R_7$ are each independently H or Y—$C_1$-$C_6$ alkyl, where Y is NH, S, Se, Si, B or O;

$R_5$, $R_8$ and $R_9$ are each independently H, CN, OH, or $C_1$-$C_6$ alkyl;

or $R_8$ and $R_9$, taken together with the atoms to which they are connected, form an aryl or heteroaryl ring; and $M^-$ is an anion.

In certain embodiments, the compound is selected from the group consisting of Oxazine 1, Oxazine 4, Oxazine 170, Oxazine 750 and Rhodamine 800.

In certain embodiments, the compound is selected from the group consisting of ESNF-35, ESNF-36, ESNF-37, ESNF-38, ESNF-39, ESNF-40, ESNF-41 and ESNF-42.

In certain embodiments, the compound is TG17, TG18, TG20, or CNN13.

In certain embodiments, the imaging agent is administered to an organism comprising the tissue or cells. In certain embodiments, the organism is human.

In certain embodiments, $M^-$ is $ClO_4^-$.

In certain embodiments, the imaging agent has peak absorbance at about 600 nm to 850 nm.

In certain embodiments, the imaging agent comprises a radioisotope for positron emission tomography.

In certain embodiments, wherein the imaging agent is selectively absorbed by nerve tissue or nerve cells and the selectivity is at least 2:1 relative to muscle cells.

In certain embodiments, the tissue or cells is imaged ex vivo.

In certain embodiments, the compound comprises a reactive linking group or a chelator moiety capable of chelating a metal atom. In certain embodiments, the chelator moiety is a DOTA, DTPA, hydrazinonicotinic acid (HYNIC), or desferoxime, or a derivative thereof.

In another aspect, the invention provides a method of imaging nerve tissue, the method comprising: (a) contacting the nerve tissue with a compound of Formula I or Ia, wherein R comprises a chelator moiety, and the chelator moiety is chelated to a metal atom; (b) detecting a signal from metal atom, thereby imaging the nerve tissue.

In certain embodiments, the metal atom is selected from the group consisting of Zr-89, Ga-68 and Rb-82, and the signal is detected by positron emission tomography.

In certain embodiments, the metal atom is selected from the group consisting of Tc-99m and In-111, and the signal is detected by single-photon emission computed tomography.

In certain embodiments, the metal atom is a lanthanide selected from the group consisting of Gd, Dy and Yb, and the signal is detected by magnetic resonance imaging.

In certain embodiments, the compound is also imaged by irradiating the nerve tissue at a wavelength absorbed by the compound, and detecting an optical signal from the irradiated nerve tissue, thereby imaging the nerve tissue.

In another aspect, the invention provides a compound represented by the formula (Formula Ia):

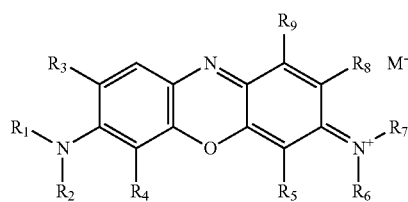

in which
$R_1$, $R_2$, $R_3$, $R_4$, $R_6$ and $R_7$ are each independently H or Y—$C_1$-$C_6$ alkyl, where Y is NH, S, Se, Si, B or O;
$R_5$, $R_8$ and $R_9$ are each independently H, CN, OH, or $C_1$-$C_6$ alkyl;

or $R_8$ and $R_9$, taken together with the atoms to which they are connected, form an aryl or heteroaryl ring; and $M^-$ is an anion.

In certain embodiments, $R_1$, $R_2$, $R_3$, $R_4$, $R_6$ and $R_7$ are each independently H, methyl or ethyl.

In certain embodiments, one of $R_5$, $R_8$ and $R_9$ is OH.

In certain embodiments, the compound is selected from the group consisting of ESNF-35, ESNF-36, ESNF-37, ESNF-38, ESNF-39, ESNF-40, ESNF-41 and ESNF-42.

In certain embodiments, the compound is TG17, TG18, TG20, or CNN13.

In certain embodiments, the compound comprises a reactive linking group or a chelator moiety capable of chelating a metal atom.

In certain embodiments, the chelator moiety is a DOTA, DTPA, hydrazinonicotinic acid (HYNIC), or desferoxime, or a derivative thereof.

In another aspect, the invention provides a pharmaceutical composition comprising a compound of Formula I or Ia (or any compound disclosed herein) and a pharmaceutically acceptable carrier.

DETAILED DESCRIPTION

Figure 1:
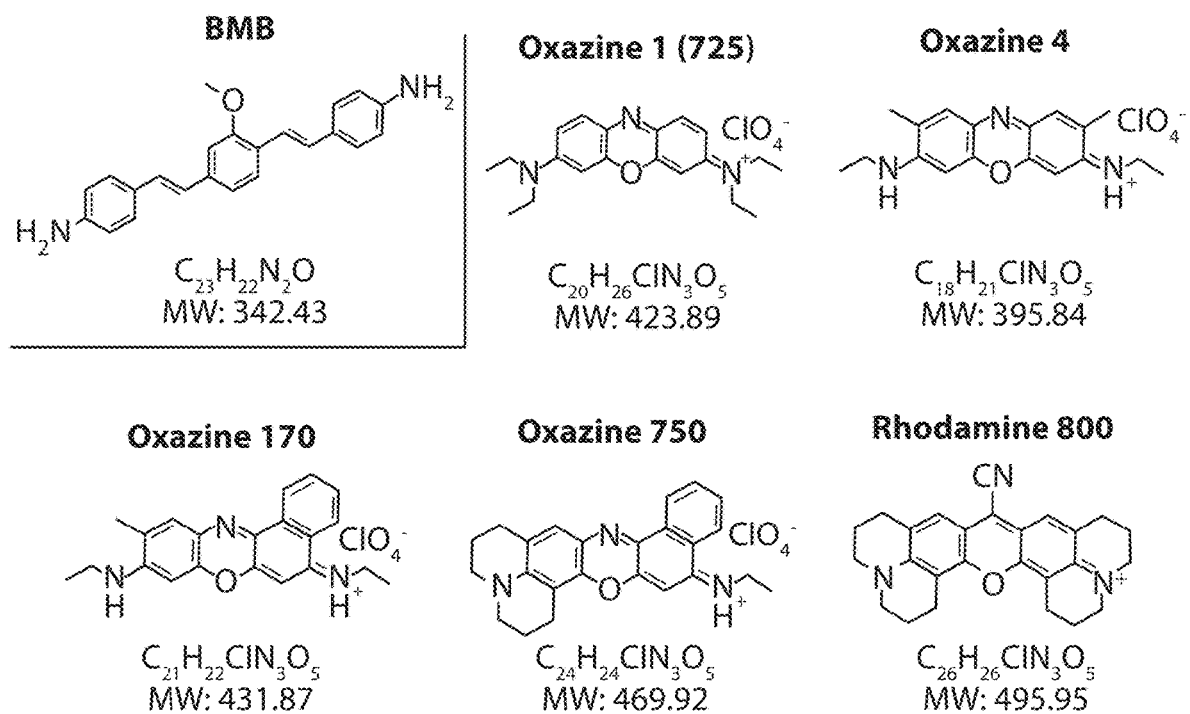
FIG. 1 shows the chemical structures of exemplary nerve-targeting fluorophores. Oxazine 1 is also known as Oxazine 725.

It has now been found that oxazine-based compounds have desirable properties of both nerve uptake and near infrared (NIR) excitation/emission. Such agents are compatible with Channel 1 (≈660 nm excitation; ≈700 nm emission) of the FLARE$^a$ Imaging System, which permits color video and NIR fluorescence to be acquired simultaneously, thus providing real-time image-guidance to surgeons about nerve location.

Definitions

The following definitions will be useful in understanding the instant invention.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used in the specification and claims, the singular form "a", "an" and "the" include plural references unless the context clearly dictates otherwise.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

As used herein, the term "subject" or "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

As used herein, the term "administration" or "administering" of the subject compound refers to providing a compound of the invention and/or prodrugs thereof to a subject in need of treatment.

As used herein, the term "carrier" refers to chemical compounds or agents that facilitate the incorporation of a compound described herein into cells or tissues.

As used herein, the term "acceptable" with respect to a formulation, composition or ingredient, as used herein, means having no persistent detrimental effect on the general health of the subject being treated.

As used herein, the term "diluent" refers to chemical compounds that are used to dilute a compound described herein prior to delivery. Diluents can also be used to stabilize compounds described herein.

The term "nerve" as used herein, includes peripheral nerve tissue and cells, including myelinated nerves. Sensory nerves and motor nerves are examples of nerve tissue.

Examples of specific nerves include the laryngeal nerve, femoral nerve, brachial plexus, sciatic nerve, pudendal nerves, penile nerves, and the like. The term "nerve tissue" also includes brain grey matter and brain white matter.

Any compositions or methods provided herein can be combined with one or more of any of the other compositions and methods provided herein.

The term "halogen", as used herein, refers to F, Cl, Br, and I.

Other definitions appear in context throughout the disclosure.

Compounds and Compositions

It has now been found that certain oxazine compounds are useful as near-infrared fluorescent nerve contrast agents.

In one aspect, the invention provides a compound represented by the formula (Formula I):

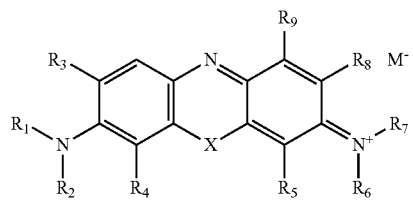

(I)

in which $R_1$, $R_2$, $R_3$, $R_4$, $R_6$ and $R_7$ are each independently H or Y—$C_1$-$C_6$ alkyl, where Y is NH, S, Se, Si, B, or O;

$R_5$, $R_8$ and $R_9$ are each independently H, CN, OH, or $C_1$-$C_6$ alkyl;

or $R_1$ and $R_3$, taken together with the atoms to which they are connected, form a 5- to 7-membered heterocylic ring;

or $R_2$ and $R_4$, taken together with the atoms to which they are connected, form a 5- to 7-membered heterocylic ring;

or $R_5$ and $R_6$, taken together with the atoms to which they are connected, form a 5- to 7-membered heterocylic ring;

or $R_7$ and $R_8$, taken together with the atoms to which they are connected, form a 5- to 7-membered heterocylic ring;

or $R_8$ and $R_9$, taken together with the atoms to which they are connected, form an aryl or heteroaryl ring;

X is O, S, Se, Si, B, N—R; where R=H or $C_1$-$C_6$ alkyl;

$M^-$ is an anion;

(b) irradiating the tissue or cells at a wavelength absorbed by the imaging agent; and (c) detecting an optical signal from the irradiated tissue or cells, thereby imaging the tissue or cells.

In certain embodiments, the tissue or cells is nerve tissue or nerve cells.

In certain embodiments, X is O.

In certain embodiments, the compound is represented by Formula Ia:

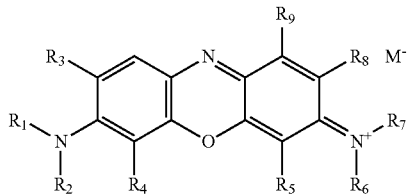

in which $R_1$, $R_2$, $R_3$, $R_4$, $R_6$ and $R_7$ are each independently H or Y—$C_1$-$C_6$ alkyl, where Y is NH, S, or O;

$R_5$, $R_8$ and $R_9$ are each independently H, CN, OH, or $C_1$-$C_6$ alkyl;

or $R_8$ and $R_9$, taken together with the atoms to which they are connected, form an aryl or heteroaryl ring;

and $M^-$ is an anion.

In certain embodiments of Formula I or Ia, $R_1$, $R_2$, $R_3$, $R_4$, $R_6$ and $R_7$ are each independently H, methyl or ethyl. In certain embodiments, one of $R_5$, $R_8$ and $R_9$ is OH.

In Formulae I and Ia, $M^-$ can be any anion compatible with the compound of Formula I or Ia. Examples of anion include halogen anions such as $F^-$, $Cl^-$, $Br^-$, or $I^-$; inorganic anions such as perchlorate, sulfate, phosphate, and the like; and anions of organic acids such as acetate, benzoate, and the like; or anions suitable for use in pharmaceutically acceptable salts as described herein. In certain embodiments, $M^-$ is halogen or $ClO_4^-$.

In certain embodiments, the compound of Formula I or Ia has a peak absorbance at about 600 nm to 850 nm.

In certain embodiments, the compound of Formula I or Ia has a log D at pH 7.4 between 0.5 and 3. In certain embodiments, the compound of Formula I or Ia has a molecular weight <500 Da.

In certain embodiments of Formula I or Ia, the compound is selected from the group consisting of ESNF-35, ESNF-36, ESNF-37, ESNF-38, ESNF-39, ESNF-40, ESNF-41 and ESNF-42:

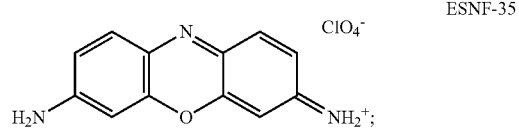

ESNF-35

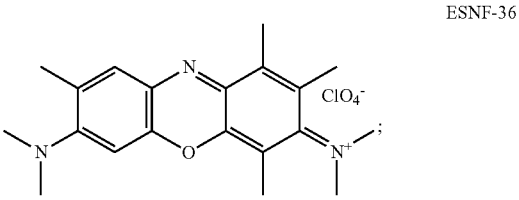

ESNF-36

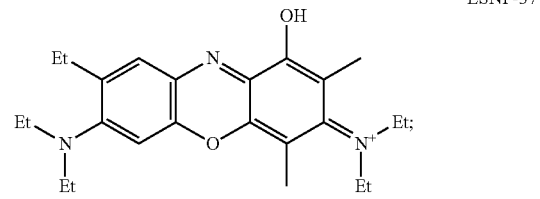

ESNF-37

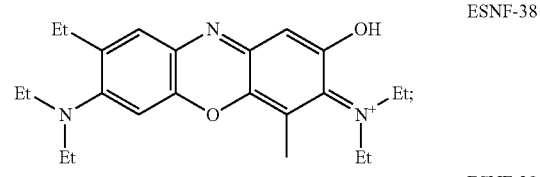

ESNF-38

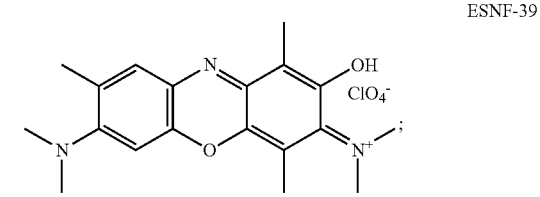

ESNF-39

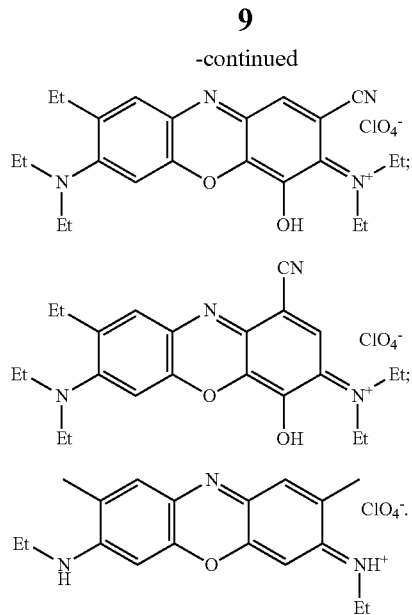

ESNF-40

ESNF-41

ESNF-42

In certain embodiments of Formula I (or Ia), the compound is Oxazine 1, Oxazine 4, Oxazine 170, Oxazine 750, TG17, TG18, TG20, or CNN13:

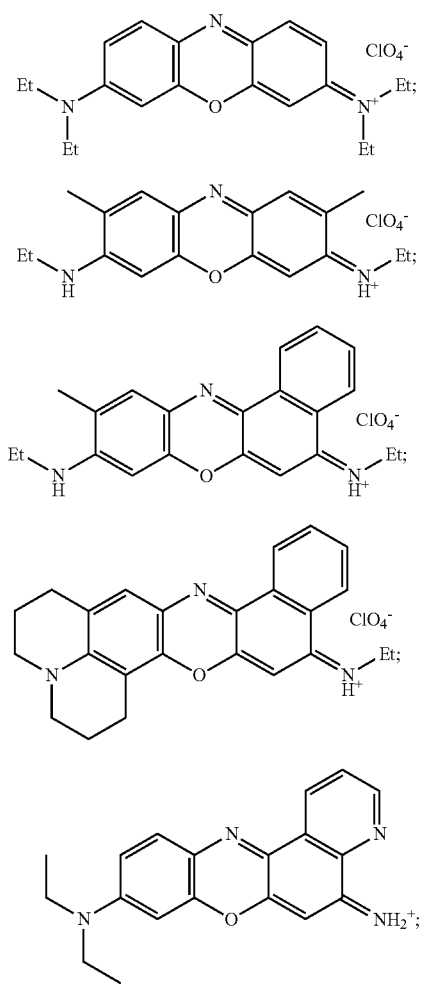

Oxazine 1

Oxazine 4

Oxazine 170

Oxazine 750

TG17

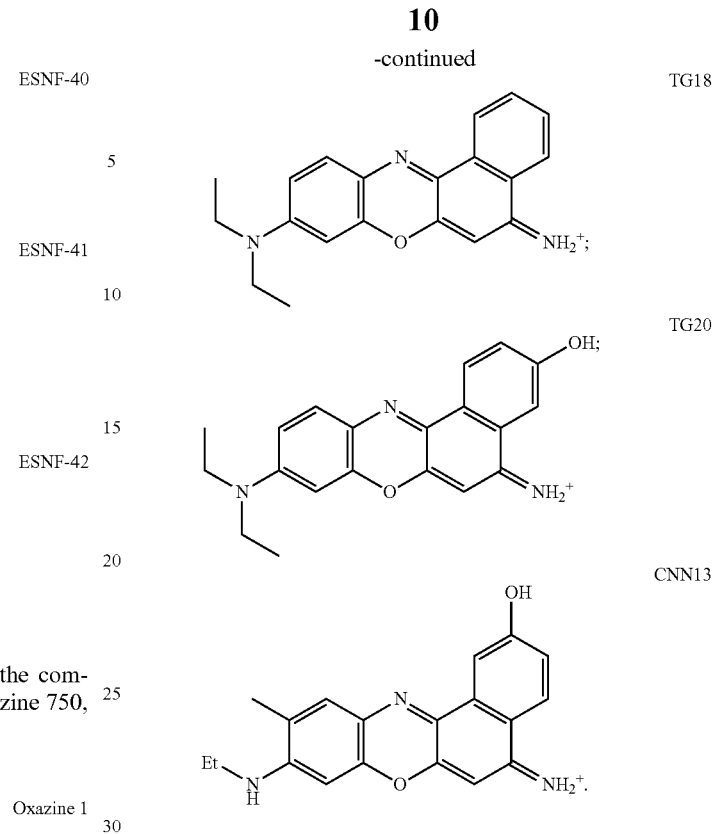

TG18

TG20

CNN13

The compound Rhodamine 800 has the following structure:

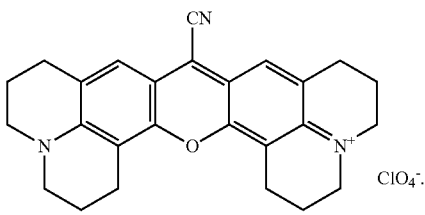 [SMILES: N#CC1=c2cc3c4c(c2Oc2c1cc1c5c2CCCN5CCC1)CCC[N+]=4CCC3]

The term "alkyl," refers to a straight or branched hydrocarbon radical having from 1-6 carbon atoms, or from 1-4 carbon atoms (unless stated otherwise) and includes, for example, methyl, ethyl, n-propyl, iso-propyl, n-butyl, sec-butyl, isobutyl, tert-butyl, n-pentyl, iso-pentyl, n-hexyl and the like. An alkyl can be unsubstituted or substituted with one or more suitable substituents.

The term "cycloalkyl" refers to a monocyclic or polycyclic hydrocarbon ring group having from 3 to 6 carbon atoms, in the hydrocarbon ring (unless stated otherwise) and includes, for example, cyclopropyl, cyclobutyl, cyclohexyl, cyclopentyl, and the like. A cycloalkyl group can be unsubstituted or substituted with one or more suitable substituents.

The term "hetero" refers to the replacement of at least one carbon atom member in a ring system with at least one heteroatom such as nitrogen, sulfur, and oxygen.

The term "heterocyclic" means a non-aromatic monocyclic ring having from 2 to 5 carbon atoms in the ring (unless stated otherwise) and at least one heteroatom, preferably, one heteroatom selected from nitrogen, sulfur (including oxidized sulfur such as sulfone or sulfoxide) and oxygen. A heterocycloalkyl group can have one or more carbon-carbon double bonds or carbon-heteroatom double bonds in the ring group as long as the ring group is not rendered aromatic by their presence.

Examples of heterocyclic groups include pyrrolidinyl, piperidinyl, tetrahydropyranyl, and the like. A heterocyclic group can be unsubstituted or substituted with one or more suitable substituents.

As used herein, the term "aryl" refers to an unsubstituted or substituted carbocyclic aromatic monocyclic group such as a phenyl group. The term "aryl" may be interchangeably used with "aryl ring".

As used herein, the term "heteroaryl: refers to an unsubstituted or substituted heterocyclic aromatic monocyclic group such as a pyridyl, furanyl, or thiophenyl group, and the like. Heteroaryl groups have 5 or 6 atoms in the heteroaromatic ring, 1 of which is independently selected from the group consisting of oxygen, sulfur and nitrogen. Typical heteroaryl groups include, for example, a pyridyl, furanyl, or thiophenyl group.

An aryl or heteroaryl can be unsubstituted or substituted with one or more suitable substituents.

A "substituent," as used herein, refers to a molecular moiety that is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. The term "substitution" refers to replacing a hydrogen atom in a molecular structure with a substituent, such that the valence on the designated atom is not exceeded, and such that a chemically stable compound (i.e., a compound that can be isolated, characterized, and tested for biological activity) results from the substitution.

As described above, certain groups can be unsubstituted or substituted with one or more suitable substituents by other than hydrogen at one or more available positions, typically 1, 2, 3, 4 or 5 positions, by one or more suitable groups (which may be the same or different). Certain groups, when substituted, are substituted with 1, 2, 3 or 4 independently selected substituents. Suitable substituents include halo, alkyl, aryl, hydroxy, alkoxy, hydroxyalkyl, amino, and the like.

In preferred embodiments, the compounds of the invention are cell-permeable. In preferred embodiments, the compounds of the invention are not significantly toxic to cells (e.g., to cells in culture or in vivo).

In certain embodiments, the imaging agent of the invention comprises a radioisotope having a single-photon or positron emission decay mode and suitable for detection by single-photon emission tomography (SPECT) or positron emission tomography (PET). Examples of suitable radioisotopes include C-11 and F-18. Such isotopes can be incorporated into a compound of the invention, e.g., by use of appropriate isotopically-enriched reagents during synthesis of the compound. Additional useful radiotracers, such as Ga-68 Zr-89, or Rb-82 (PET), or Tc-99m (SPECT), can be attached to the compound through a radiometal chelator such as 1,4,7,10-tetraazacyclododecane-1,4,7,10-tetraacetic acid (DOTA), diethylene triamine pentaacetic acid (DTPA), hydrazinonicotinic acid (HYNIC), or desferoxime, respectively (or derivatives thereof). Chelator moieties can be covalently attached to an oxazine compound, e.g., through a linking atom or group, e.g., by acylation of a hydroxyl group of a compound of Formula I or Ia with a carboxylate group of a chelator such as DOTA. By incorporation of an appropriate PET- or SPECT-detectable isotope, a compound according to the invention can be detected using SPECT or PET imaging (e.g., even when administered at a low dose), e.g., using a conventional SPECT or PET imaging system, while also being detectable optically (e.g., by fluorescence imaging), e.g., when administered at a higher dose. Dual-mode optical and SPECT or PET imaging is also possible using such compounds. Similarly, imaging by magnetic resonance imaging (MRI), including dual-mode optical/MRI imaging, can be performed by using a compound of the invention comprising a lanthanide (such as $Yb^{3+}$, $Dy^{3+}$ or $Gd^{3+}$), e.g., by chelating the lanthanide ion using a suitable chelating moiety.

Compounds of the invention can be prepared using a variety of methods, some of which are known in the art. For example, the compounds can be prepared using conventional methods of synthetic organic chemistry (see, e.g., Michael B. Smith, "March's Advanced Organic Chemistry: Reactions, Mechanisms, and Structure, 7th Edition", Wiley (2013)).

For example, oxazine compounds of Formula I or Ia can be prepared by the route shown in Scheme 1:

Scheme 1:

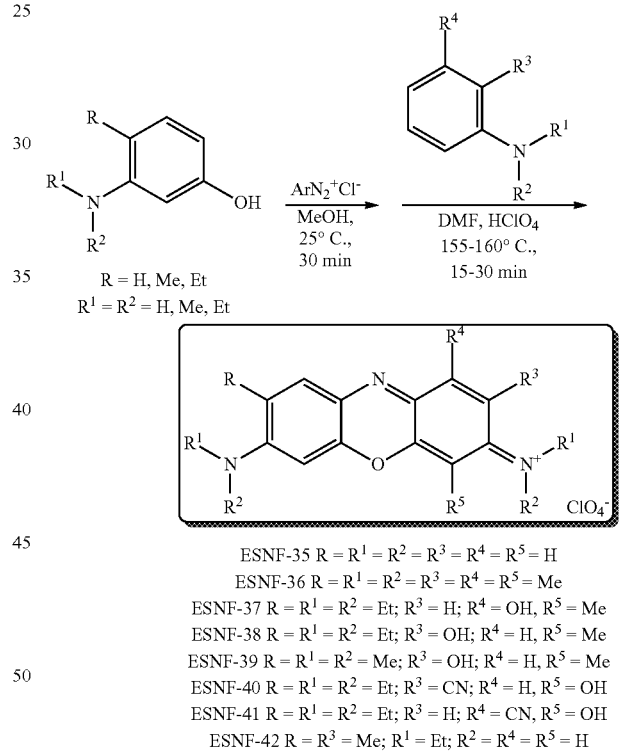

ESNF-35 R = $R^1$ = $R^2$ = $R^3$ = $R^4$ = $R^5$ = H
ESNF-36 R = $R^1$ = $R^2$ = $R^3$ = $R^4$ = $R^5$ = Me
ESNF-37 R = $R^1$ = $R^2$ = Et; $R^3$ = H; $R^4$ = OH, $R^5$ = Me
ESNF-38 R = $R^1$ = $R^2$ = Et; $R^3$ = OH; $R^4$ = H, $R^5$ = Me
ESNF-39 R = $R^1$ = $R^2$ = Me; $R^3$ = OH; $R^4$ = H, $R^5$ = Me
ESNF-40 R = $R^1$ = $R^2$ = Et; $R^3$ = CN; $R^4$ = H, $R^5$ = OH
ESNF-41 R = $R^1$ = $R^2$ = Et; $R^3$ = H; $R^4$ = CN, $R^5$ = OH
ESNF-42 R = $R^3$ = Me; $R^1$ = Et; $R^2$ = $R^4$ = $R^5$ = H

As shown in Scheme 1, a substituted aminophenol (some of which are commercially available) can be reacted with an aryl diazonium salt, followed by reaction with a substituted aminobenzene to yield oxazine compounds.

In another aspect, the invention provides pharmaceutical compositions of a compound of Formula I or Ia.

For the therapeutic uses of compounds provided herein, including compounds of Formula I or Ia, or pharmaceutically acceptable salts, solvates, N-oxides, prodrugs, or isomers thereof, such compounds are administered in therapeutically effective amounts either alone or as part of a pharmaceutical composition. Accordingly, provided herein are pharmaceutical compositions, which comprise at least one compound provided herein, including at least one compound of Formula I or Ia, pharmaceutically acceptable salts and/or solvates thereof, and one or more pharmaceutically acceptable carriers, diluents, adjuvant or excipients. The methods of administration of such compounds and compositions include, but are not limited to, intravenous administration, inhalation, oral administration, rectal administration, parenteral, intravitreal administration, subcutaneous administration, intramuscular administration, intranasal administration, dermal administration, topical administration, ophthalmic administration, buccal administration, tracheal administration, bronchial administration, sublingual administration or optic administration. Compounds provided herein are administered by way of known pharmaceutical formulations, including tablets, capsules or elixirs for oral administration, suppositories for rectal administration, sterile solutions or suspensions for parenteral or intramuscular administration, lotions, gels, ointments or creams for topical administration, and the like.

The amount administered will vary depending on, among others, the tissue or organ to be imaged, the age and relative health of the subject, the potency of the compound administered, the mode of administration and the like.

Pharmaceutically acceptable salt forms include pharmaceutically acceptable acidic/anionic or basic/cationic salts. Pharmaceutically acceptable acidic/anionic salts include acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts. Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

A pharmaceutically acceptable acid salt is formed by reaction of the free base form of a compound of Formula I or Ia with a suitable inorganic or organic acid including, but not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid. A pharmaceutically acceptable acid addition salt of a compound of Formula I or Ia can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

The free acid or free base forms of the compounds of the invention may be prepared from the corresponding base addition salt or acid addition salt form, respectively. For example a compound of the invention in an acid addition salt form may be converted to the corresponding free base form by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Prodrug derivatives of the compounds of the invention may be prepared by methods known to those of ordinary skill in the art (e.g., for further details see Saulnier et al., Bioorg. Med. Chem. Letters, 1994, 4, 1985; the entire teachings of which are incorporated herein by reference).

Protected derivatives of the compounds of the invention may be prepared by means known to those of ordinary skill in the art. A detailed description of techniques applicable to the creation of protecting groups and their removal can be found in T. W. Greene, "Protecting Groups in Organic Chemistry," 3rd edition, John Wiley and Sons, Inc., 1999, the entire teachings of which are incorporated herein by reference.

Compounds of the invention may be prepared as their individual stereoisomers by reaction of a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubility, reactivity, etc.) and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet and Samuel H. Wilen, "Enantiomers, Racemates and Resolutions," John Wiley And Sons, Inc., 1981, the entire teachings of which are incorporated herein by reference.

Suitable pharmaceutically acceptable carriers, diluents, adjuvants, or excipients for use in the pharmaceutical compositions of the invention include tablets (coated tablets) made of for example collidone or shellac, gum Arabic, talc, titanium dioxide or sugar, capsules (gelatin), solutions (aqueous or aqueous-ethanolic solution), syrups containing the active substances, emulsions or inhalable powders (of various saccharides such as lactose or glucose, salts and mixture of these excipients with one another) and aerosols (propellant-containing or -free inhale solutions).

Excipients which may be used include, for example, water, pharmaceutically acceptable organic solvents such as paraffins (e.g., petroleum fractions), vegetable oils (e.g. groundnut or sesame oil), mono- or polyfunctional alcohols (e.g., ethanol or glycerol), carriers such as natural mineral powders (e.g., kaoline, clays, talc, chalk), synthetic mineral powders (e.g., highly dispersed silicic acid and silicates), sugars (e.g., cane sugar, lactose and glucose), emulsifiers (e.g., lignin, spent sulphite liquors, methylcellulose, starch and polyvinylpyrrolidone) and lubricants (e.g., magnesium stearate, talc, stearic acid and sodium lauryl sulphate).

Exemplary methods for preparing the compounds of the invention are described herein, including in the Examples.

Methods

The present invention features various methods using the near-infrared fluorescent nerve contrast agents described herein.

In one aspect, the invention provides a method of imaging tissue or cells, the method comprising:

(a) contacting the tissue or cells with an imaging agent represented by the formula (Formula I):

$$\text{(I)}$$

in which
$R_1$, $R_2$, $R_3$, $R_4$, $R_6$ and $R_7$ are each independently H or Y—$C_1$-$C_6$ alkyl, where Y is NH, S, Se, Si, B, or O;
$R_5$, $R_8$ and $R_9$ are each independently H, CN, OH, or $C_1$-$C_6$ alkyl;
  or $R_1$ and $R_3$, taken together with the atoms to which they are connected, form a 5- to 7-membered heterocylic ring;
  or $R_2$ and $R_4$, taken together with the atoms to which they are connected, form a 5- to 7-membered heterocylic ring;
  or $R_5$ and $R_6$, taken together with the atoms to which they are connected, form a 5- to 7-membered heterocylic ring;
  or $R_7$ and $R_8$, taken together with the atoms to which they are connected, form a 5- to 7-membered heterocylic ring;
  or $R_8$ and $R_9$, taken together with the atoms to which they are connected, form an aryl or heteroaryl ring;
X is O, S, Se, Si, B, N—R; where R=H or $C_1$-$C_6$ alkyl;
$M^-$ is an anion;
(b) irradiating the tissue or cells at a wavelength absorbed by the imaging agent; and
(c) detecting an optical signal from the irradiated tissue or cells, thereby imaging the tissue or cells.

In certain embodiments, the tissue or cells is nerve tissue or nerve cells.

In certain embodiments, X is O.

In certain embodiments, the compound (imaging agent) is represented by Formula Ia:

in which
$R_1$, $R_2$, $R_3$, $R_4$, $R_6$ and $R_7$ are each independently H or Y—$C_1$-$C_6$ alkyl, where Y is NH, S, or O;
$R_5$, $R_8$ and $R_9$ are each independently H, CN, OH, or $C_1$-$C_6$ alkyl;
  or $R_8$ and $R_9$, taken together with the atoms to which they are connected, form an aryl or heteroaryl ring; and
$M^-$ is an anion.

In certain embodiments, the compound is selected from the group consisting of Oxazine 1, Oxazine 4, Oxazine 170, Oxazine 750 and Rhodamine 800.

In certain embodiments, the compound is selected from the group consisting of ESNF-35, ESNF-36, ESNF-37, ESNF-38, ESNF-39, ESNF-40, ESNF-41 and ESNF-42.

In certain embodiments, the compound is TG17, TG18, TG20, or CNN13.

In certain embodiments, the imaging agent is administered to an organism comprising the tissue or cells.

In certain embodiments, the organism is human.

In certain embodiments of Formula I or Ia, $M^-$ is $ClO_4^-$.

In certain embodiments of Formula I or Ia, the imaging agent has peak absorbance at about 600 nm to 850 nm. Compounds that possess absorbance at the lower NIR (700-850 nm), are referred to herein as herein "near-infrared fluorescent moieties".

In certain embodiments, the imaging agent (a) has an extinction coefficient of at least 100,000 $M^{-1}$ $cm^{-1}$ in aqueous medium, (b) has an $LD_{50}$ of at least 100 mg/Kg in humans, and (c) has a half-life in the human body of at least 10 minutes.

The imaging agents can have a "signal-to-background ratio" (SBR) suitable to permit fluorescence detection. SBR is a measure of the intensity of the fluorescent signal obtained from a target (peak signal) over the measure of the intensity of the fluorescent signal obtained nearby the target (background signal), the target being the tissues or cells targeted by the imaging agent. SBR measurements can be readily obtained through routine measurement procedures. For fluorescent imaging systems, and other optical-type systems, digital images recording optical signals of the target facilitate SBR measurement. Higher SBR values are more desirable, resulting in greater resolution of the imaged tissues. In some embodiments, the imaging agents achieve an SBR of at least about 1.1 (i.e., peak signal is at least 10% over background). In further embodiments, the imaging agents achieve an SBR of at least about 1.2, at least about 1.3, at least about 1.4, at least about 1.5, at least about 1.6, at least about 1.7, at least about 1.8, at least about 1.9, or at least about 2.0. In yet further embodiments, the imaging agents achieve an SBR of about 1.1 to about 50, about 1.5 to about 30, about 2.0 to about 20, about 2.0 to about 5.0, or about 5.0 to about 10.

The imaging agents generally include one or more ionic groups. In some embodiments, the imaging agents include two or more, three or more, four or more, or five or more ionic groups. Ionic groups serve to increase solubility of the generally hydrophobic dye portions of the imaging agent, thus improving biodistribution. The ionic groups can be located on any portion of the imaging agent.

The steps of irradiating the tissue or cells at a wavelength absorbed by the imaging agent, and detecting an optical signal from the irradiated tissue or cells, thereby imaging the tissue or cells, can be performed using an imaging system such as the FLARE™ Image-Guided Surgery System, which is a continuous-wave (CW) intraoperative imaging system that is capable of simultaneous, real-time acquisition and display of color video (i.e., surgical anatomy) and two channels of invisible NIR fluorescent (700 nm and 800 nm) light (see, e.g., Gioux et al., *Mol. Imaging.* 9(5): 237-255 (2010) and U.S. Pat. No. 8,473,035 to Frangioni, for a description of suitable systems). With FLARE™ and other NIR fluorescence imaging systems, contrast agent emission wavelength in the 800-850 nm range is preferred whenever possible because of lower autofluorescence and lower attenuation from both absorbance and scatter when compared to emission near 700 nm. Nevertheless, fluorophores emitting within Channel 1 (≈700 nm) of the FLARE™ imaging system still retain the benefits of NIR fluorescence imaging, including detection of nerves below the surface of blood and tissue.

In some embodiments, the imaging agents can be formulated into pharmaceutically acceptable formulations and administered intravenously to an organism for imaging. The dosed organism can be imaged using, for example, the FLARE™ system. The imaging system can irradiate the dosed organism with radiation absorbed by the imaging agent, and detect optical signals, such as NIR fluorescence, emanating from the targeted portions of the organism containing the imaging agent. The detected signals can be recorded and analyzed by obtaining digital images or video of the subject organism, thereby facilitating diagnostic procedures and image-guided medical techniques.

The invention also provides methods of performing image-guided surgery, the methods comprising imaging nerve tissue or cells according to a method described herein, and then performing surgery such that nerve tissue or cells are either removed or are preserved, depending on the goals of the surgical intervention. In certain preferred embodiments, the nerve-specific contrast agent is injected intravenously to ensure that all nerves are labeled, and imaging is performed after sufficient time has passed for biodistribution to nerves and clearance of surrounding background signal.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Materials and Methods

Optical Property Measurements

Oxazine derivatives were obtained from Fisher Scientific Inc. (Pittsburgh, Pa.) or Sigma-Aldrich (Saint Louis, Mo.), and BMB was synthesized as described previously (25). Optical measurements were performed at 37° C. in phosphate-buffered saline (PBS), pH 7.4 or 100% fetal bovine serum (FBS) buffered with 50 mM HEPES, pH 7.4. Absorbance and fluorescence emission spectra were measured using fiber optic HR2000 absorbance (200-1100 nm) and USB2000FL fluorescence (350-1000 nm) spectrometers (Ocean Optics, Dunedin, Fla.). NIR excitation was provided by a 532 nm green laser pointer (Opcom Inc., Xiamen, China) set to 5 mW and coupled through a 300 m core diameter, NA 0.22 fiber (Fiberguide Industries, Stirling, N.J.). In silico calculation of the partition coefficient (log D at pH 7.4) was calculated using Marvin and J Chem calculator plugins (ChemAxon, Budapest, Hungary). Chemical similarities were calculated by Instant J Chem 6.04 using "Chemical Hashed Fingerprint" with the Normalized Euclidean dissimilarity screening configuration (ChemAxon).

NIR Fluorescence Imaging System

The dual-NIR channel FLARE$^a$ imaging system has been described in detail previously (26-28). In this study, a 670 nm excitation was used at a fluence rate of 4 mW/cm$^2$, with white light (400-650 nm) at 40,000 1×. Color and NIR fluorescence images were acquired simultaneously with custom software at rates up to 15 Hz over a 15 cm diameter field of view. A pseudo-colored lime green was used for NIR fluorescence in the color-NIR merged images. The imaging system was positioned at a distance of 18 inches from the surgical field.

Ex Vivo Nerve-Specific Fluorophore Screening

Sciatic nerves from female Yorkshire pigs were harvested, fixed in 2% paraformaldehyde (PFA), and flash frozen in optimal cutting temperature (OCT) compound using liquid nitrogen. Nerve tissues were cut in cross section using a cryostat at 10 m thickness onto positively charge glass slides. Tissue sections were washed once with phosphate buffered saline (PBS) for 2 min to remove residual OCT. The tissue was then fixed to the slide with 2% PFA for 15 min, followed by washing with PBS (3×5 min). A formulation was previously developed for intravenous (IV) administration and was used in the current study to incubate the fluorophores with the nerve tissue (25). All fluorophores were mixed from the 100 mM stock solution into the IV formulation at 100 M and incubated with the washed nerve tissue sections at room temperature for 20 min. Additional IV formulation not containing fluorophore was mixed and used to wash each nerve section twice (5 min per wash) following incubation with the formulated fluorophore. The nerve section was then washed an additional 2 times with PBS (5 min per each), after which coverslips were mounted using Fluoromount-G (Southern Biotech, Birmingham, Ala.).

NIR fluorescence microscopy for ex vivo nerve tissue slides was performed on a Nikon Eclipse TE300 microscope system as previously described (12, 19, 25). The microscope was equipped with a 100 W mercury light source, NIR-compatible optics, and a NIR-compatible 10× Plan Fluor objective lens and a 100× Plan Apo oil immersion objective lens (Nikon, Melville, N.Y.). Images were acquired on an Orca-AG (Hamamatsu, Bridgewater, N.J.). Image acquisition and analysis was performed using IPLab software (Scanalytics, Fairfax, Va.). A custom filter set (Chroma Technology Corporation, Brattleboro, Vt.) composed of a 650±22 nm excitation filter, a 675 nm dichroic mirror, and an 710±25 nm emission filter were used to detect Oxazine derivatives and Rhodamine 800 signals in the nerve tissue slides. For BMB, a mercury light source was passed through a 360±25 nm BP excitation filter, a 400 nm LP beam splitter, and a 550±50 nm emission filter.

Animal Models

Animals were housed in an AAALAC-certified facility. Animal studies were performed under the supervision of Beth Israel Deaconess Medical Center's Institutional Animal Care and Use Committee (IACUC) in accordance with approved institutional protocols (#101-2011 for rodents and #046-2010 for pigs). Male CD-1 mice weighing ≈25 g and Sprague-Dawley rats weighing ≈200 g (Charles River Laboratories, Wilmington, Mass.) were anesthetized with 100 mg/kg ketamine and 10 mg/kg xylazine intraperitoneally (Webster Veterinary, Fort Devens, Mass.). 3 female Yorkshire pigs (E. M. Parsons and Sons, Hadley, Mass.) averaging 37 kg were induced with 4.4 mg/kg intramuscular Telazol (Fort Dodge Labs, Fort Dodge, Iowa), intubated, and maintained with 2% isoflurane (Baxter Healthcare Corp., Deerfield, Ill.). Following anesthesia, electrocardiogram, heart rate, pulse oximetry, and body temperature were monitored throughout surgery.

Intraoperative Nerve-Targeting and Imaging

Initial in vivo screening occurred in rats based on our previous study of BMB (Supplementary Methods) (25). For kinetic and dose-response studies, 50-400 nmol (0.8-6.3 mg/kg) of Oxazine 4 was injected intravenously into mice and measurements taken over 24 h. Control images were acquired prior to injecting NIR fluorophores. The fluorescence signal in nervous tissues and signal-to-background ratio (SBR) compared to neighboring muscle (Mu) were obtained over the period of imaging. For the large animal study, the optimal dose found in mice (200-400 nmol per mouse) was used in pigs by scaling to body surface area (29, 30). 20-40 mol (0.17-0.34 mg/kg) of Oxazine 4 was injected intravenously into Yorkshire pigs and the fluorescence images of RLN, BP, and SN were observed in real-time using the FLARE$^a$ imaging system up to 4 h post-injection (N=5 subjects).

Quantitation and Statistical Analysis

The fluorescence intensity (FI) and background (BG) intensity of a region of interest (ROI) over each nerve/tissue were calculated and quantified using custom FLARE$^a$ software. The FI of the RLN, BP, and SN at the optimal dose and time point were quantified to measure tissue-specific targeting. Adjacent tissues such as trachea (Tr), thyroid (Th), tracheoesophageal groove (TEG), muscle (Mu), and adipose tissue (Ad) were used as background to calculate the SBR of RLN, BP, and SN in pigs. Statistical analysis was carried out using a one-way ANOVA followed by Tukey's multiple comparisons test. Results were presented as mean±S.D. and curve fitting was performed using Prism version 4.0a software (GraphPad, San Diego, Calif.).

Hematoxylin and Eosin (H&E) Histology and NIR Fluorescence Microscopy RLN, BP, and SN were extracted from pigs 4 h post-injection and placed in 2% paraformaldehyde in PBS for 30 min before mounting in Tissue-Tek OCT compound (Fisher Scientific, Pittsburgh, Pa.) and flash-freezing in liquid nitrogen. Frozen samples were cryosectioned (10 μm per slice); 1 slide was stained with H&E and a consecutive section was used for fluorescence microscopy. NIR fluorescence microscopy was performed as described above for the ex vivo assay.

Optical Property Measurements:

All optical measurements were performed at 37° C. in phosphate-buffered saline (PBS), pH 7.4, 100% fetal bovine serum (FBS) buffered with 50 mM HEPES, pH 7.4, methanol (MeOH), or dimethyl sulfoxide (DMSO). Absorbance and fluorescence emission spectra of the series of NIR fluorophores were measured using fiber optic HR2000 absorbance (200-1100 nm) and USB2000FL fluorescence (350-1000 nm) spectrometers (Ocean Optics, Dunedin, Fla.). Excitation light was provided by a 532 nm green laser pointer (Opcom Inc., Xiamen, China) set to 5 mW and coupled through a 300 μm core diameter, NA 0.22 fiber (Fiberguide Industries, Stirling, N.J.). In silico calculation of the partition coefficient (log D at pH 7.4) was calculated using Marvin and J Chem calculator plugins (ChemAxon, Budapest, Hungary).

In Vivo Nerve-Specificity Screening:

Sprague-Dawley (SD) male rats weighing 250-300 g were purchased from Charles River Laboratories (Wilmington, Mass.). BMB, Oxazine 1, Oxazine 4, Oxazine 170, Oxazine 750, and Rhodamine 800 were initially screened to investigate nerve specificity in rats. For the initial screening, we administered a relatively high dose (2 mg/kg; 1 μmol) of each fluorophore intravenously. 4 h after injection, brachial plexus (BP) and sciatic nerve (SN) were imaged using the intraoperative FLARE$^a$ system for in vivo nerve-specific fluorophores screening.

Results

Chemical and Optical Properties

Figure 6A:
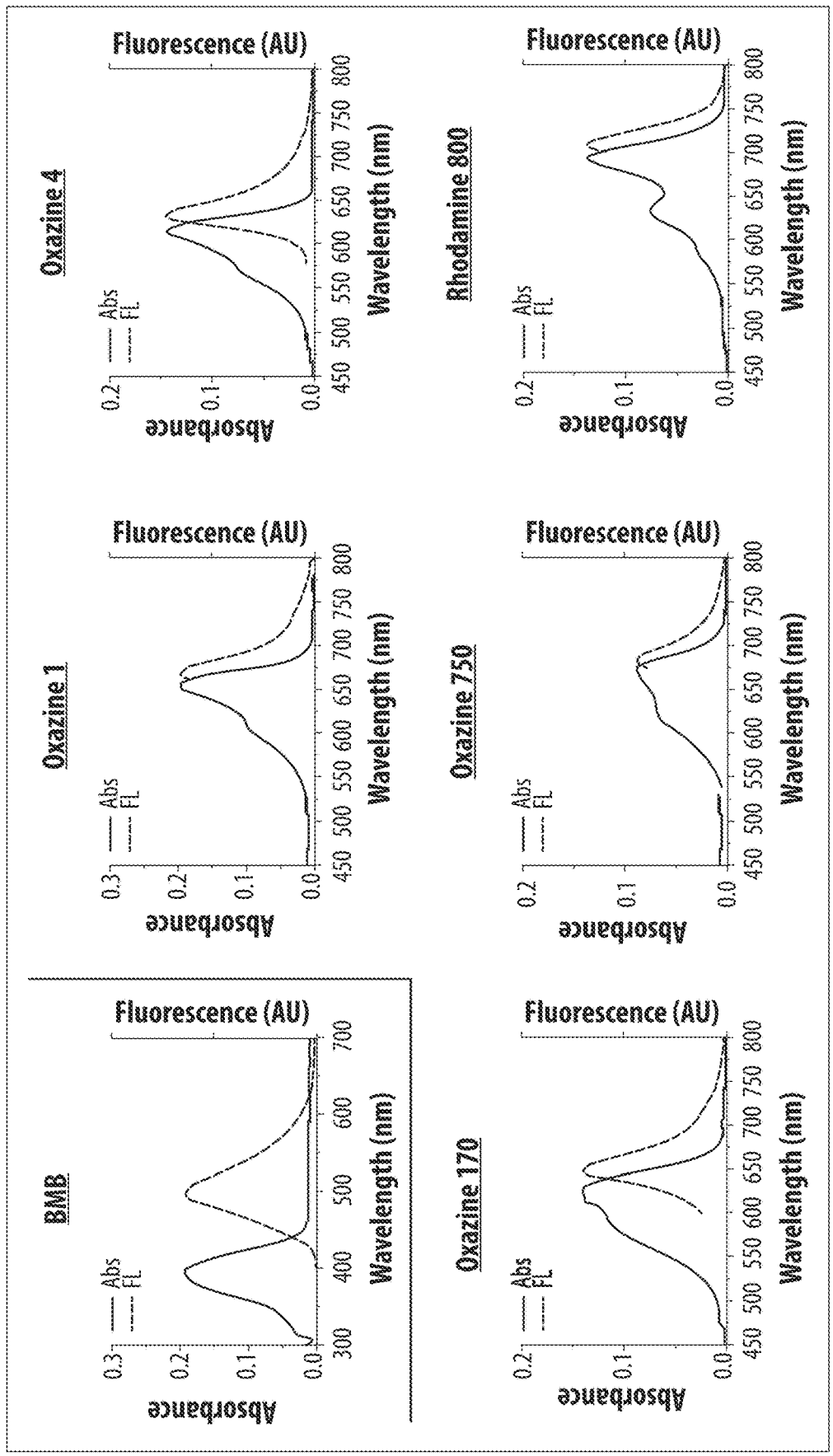
FIG. 6 shows: A) Optical Properties of Nerve-Targeting Fluorophores. Absorbance and fluorescence spectra were obtained at a concentration of 1 M in 100% FBS supplemented with 50 mM HEPES, pH 7.4. B) Optical properties of Oxazine 4 were measured in PBS (pH 7.4), FBS (pH 7.4), MeOH, and DMSO.

As shown in FIG. 1, a series of symmetric Oxazine derivatives having cationic pendant groups were explored for nerve cell-specific targeting ex vivo and in vivo. BMB (ultraviolet excitation, visible emission) was used as a positive control. Oxazine 1 and Oxazine 4 have relatively high extinction coefficients (>140,000 $M^{-1}$ $cm^{-1}$) and a moderate Stokes' shift (>17 nm) in 100% serum, pH 7.4 (Table 1 and FIG. 6). The log D at pH 7.4 of BMB, Oxazine 170, and Oxazine 750 are higher than 3.5, while Oxazine 1 and Rhodamine 800 had values less than 1. The log D at pH 7.4 of Oxazine 4 was 3.38 with a MW of 395.84 (Table 1 and FIG. 6).

TABLE 1

Chemical and Physical Properties of Nerve-Targeting Fluorophores.

| Fluorophore | MW (Da) | LogD, pH 7.4 | PSA (Å$^2$) | HBD/ HBA | Rotatable Bonds | λ ($M^{-1}cm^{-1}$) | Abs (nm) | Em (nm) |
|---|---|---|---|---|---|---|---|---|
| BMB | 364.06 | 4.84 | 61.27 | 2/3 | 5 | 52,800 | 397 | 498 |
| Oxazine 1 | 423.89 | 0.33 | 27.84 | 0/3 | 5 | 196,000 | 655 | 670 |
| Oxazine 4 | 395.84 | 3.38 | 47.59 | 2/3 | 3 | 143,000 | 616 | 635 |
| Oxazine 170 | 431.87 | 3.94 | 47.59 | 2/3 | 3 | 69,000 | 625 | 650 |
| Oxazine 750 | 469.92 | 4.67 | 38.80 | 1/3 | 1 | 44,000 | 676 | 684 |
| Rhodamine 800 | 495.95 | 0.43 | 39.27 | 0/3 | 0 | 68,000 | 697 | 710 |

MW = molecular weight; PSA = polar surface area; HBD/HBA = H bond donors/acceptors; λ = extinction coefficient; QY = quantum yield; Abs = peak absorbance; Em = peak emission.

Ex Vivo Nerve-Specific Fluorophores Screening

Figure 2:
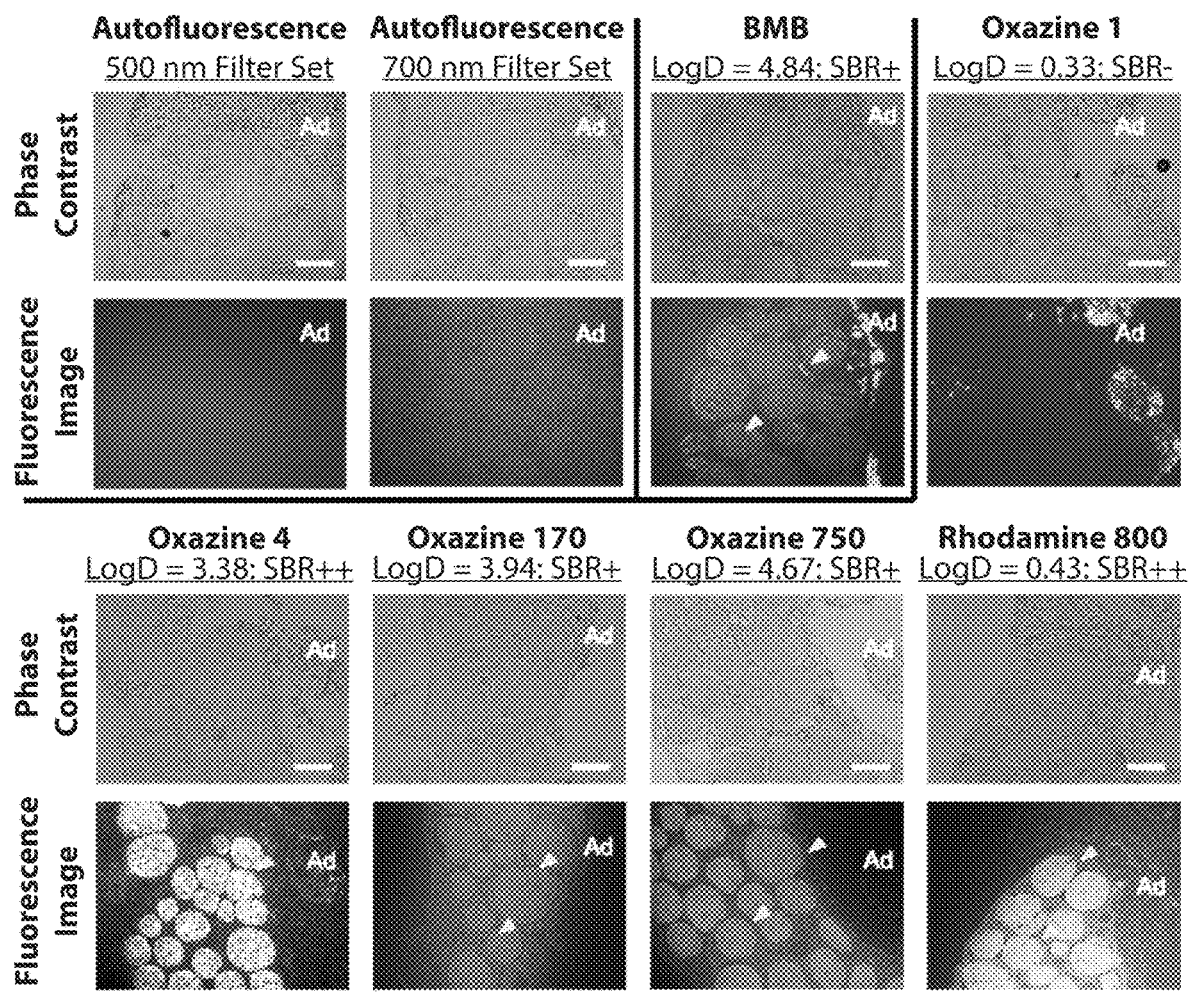
FIG. 2 shows the results of an ex vivo screening assay of fluorophores for nerve-specificity. Phase contrast image (top) and fluorescence image (bottom) of nerve tissue sections incubated with 100 μM of test fluorophores are shown. Nerve-specific fluorescence intensity was determined using staining of pig sciatic nerve cut in cross section. Nerve tissue sections were incubated in 30% FBS solutions without (negative control, autofluorescence only) and with each fluorophore. As a positive control, previously reported nerve-specific BMB was used. Shown are phase contrast image (top) and fluorescence image (bottom) of nerve tissue sections incubated with 100 μM of each fluorophore. The control autofluorescence images were taken with equivalent exposure time and normalization. Arrowheads indicate fluorescence signals in nerve bundles. Ad=adipose tissue. Scale bars=200 μm. The SBR of each nerve relative to the neighboring adipose tissue was quantified and labeled as—, SBR<1; +, SBR=1–2; and ++, SBR >2.

BMB, Oxazine 1, Oxazine 4, Oxazine 170, Oxazine 750, and Rhodamine 800 fluorophores were screened for nerve cell-specific fluorescence and undesired adipose uptake using cross sections of pig sciatic nerve tissue. Fluorescence images of Oxazine derivatives were compared with the previously identified nerve cell-specific fluorophore BMB (positive control), and nerve sections incubated in saline without fluorophores were used as negative controls for autofluorescence. As shown in FIG. 2, Oxazine 4, Oxazine 750, and Rhodamine 800 fluorophores exhibited strong fluorescence signal throughout the cross-sectioned nerve, while Oxazine 170 showed weak nerve-specific fluorescence signal. Although BMB showed relatively high fluorescence signal in the nerve, the fluorescence in adipose tissues was even higher than the target signal (SBR<1). Nerve sections incubated with Oxazine 1 fluorophore did not show any nerve-specific fluorescence signal and showed adipose-specific fluorescence signal only. From this ex vivo nerve-specific screening Oxazine 4, Oxazine 750, and Rhodamine 800 were identified as the potential candidates high performance in vivo.

In Vivo Nerve-Specific Fluorophores Screening

Figure 7:
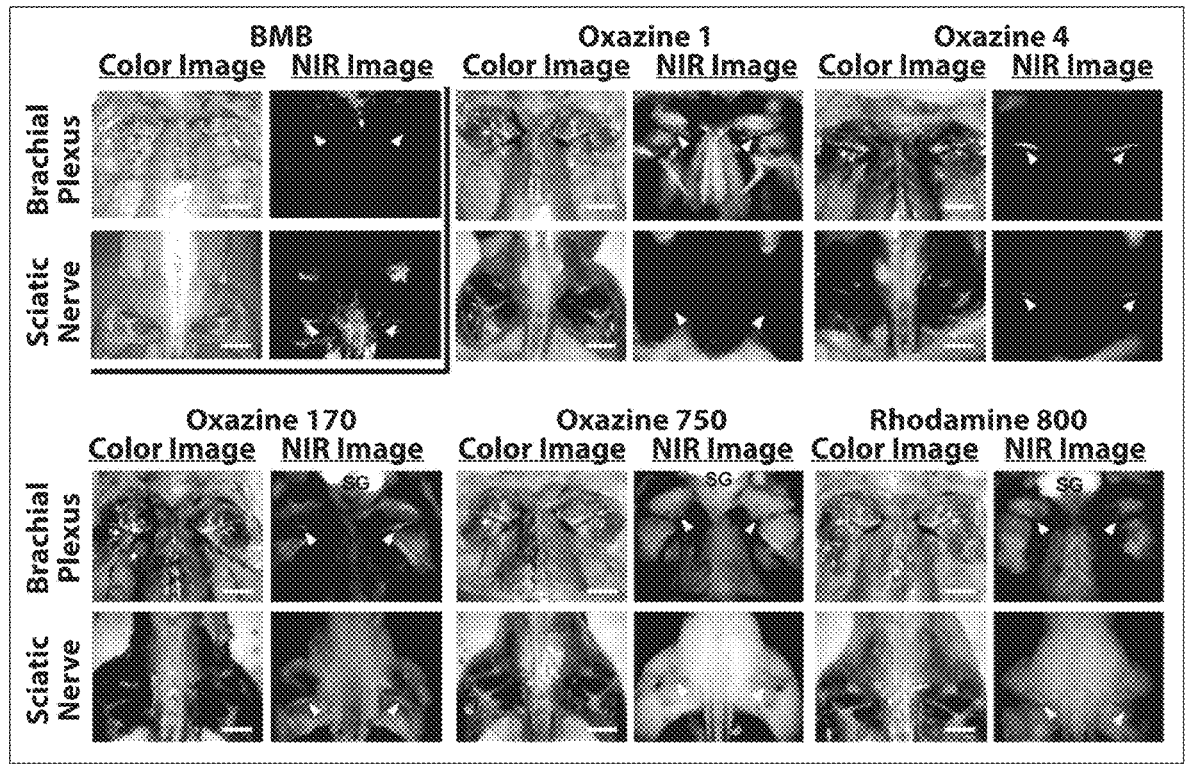
FIG. 7 shows the results so of an in vivo screening assay of fluorophores for nerve specificity. All fluorophores used in ex vivo screening were tested for in vivo nerve-specific fluorescence in the rat brachial plexus (top rows) and sciatic nerves (bottom rows). Among nerve highlighting fluorophores (BMB, Oxazine 4, and Oxazine 170), Oxazine 4 showed higher nerve-specific fluorescence signal and lower background (muscle and adipose tissue) fluorescence signal than Oxazine 170 and BMB. Arrowheads indicate fluorescence signals in nerve tissue. SG=salivary gland; scale bars=1 cm. All NIR fluorescence images have identical exposure and normalizations.
Figure 8:
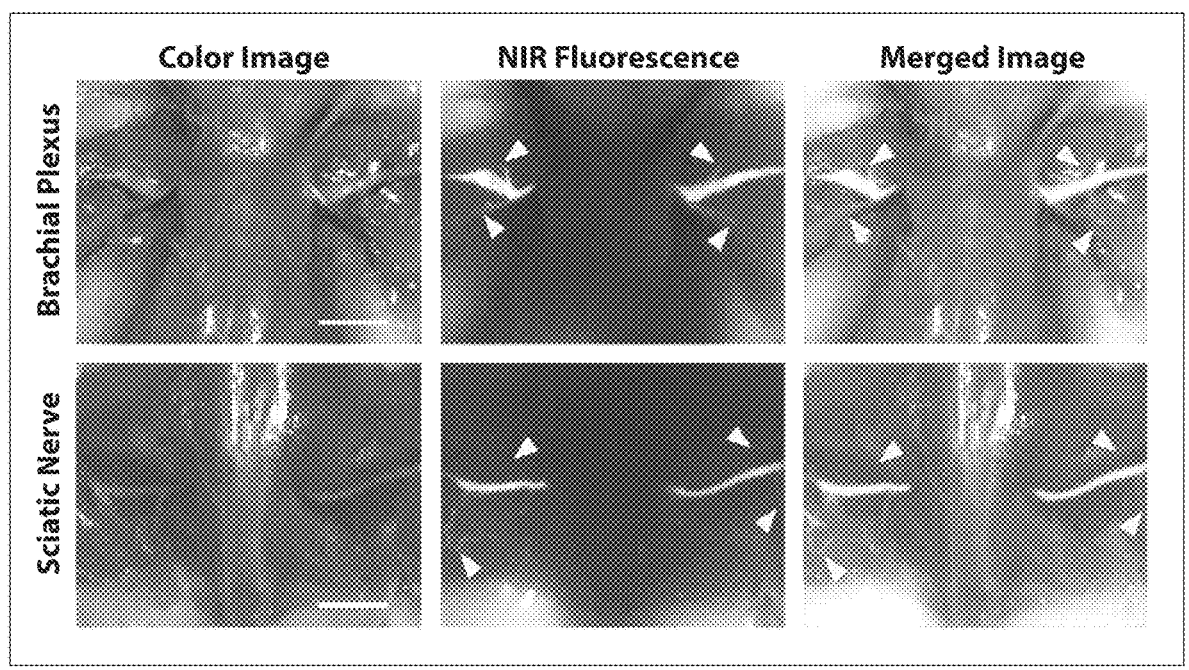
FIG. 8 shows the results so of in vivo nerve specific targeting using Oxazine 4. 1 μmol of Oxazine 4 was injected intravenously into SD rats (N=3) 4 h prior to imaging. Shown are color image, 700 nm NIR fluorescence, and a merged image of the two (pseudo-colored in lime green) acquired using the FLARE' imaging system. Arrowheads indicate small branches of main nerves, which cannot be seen in color image. All NIR fluorescence images have identical exposure and normalizations. Scale bars=1 cm.

Initial screening of fluorophore performance in vivo utilized a relatively high dose (2 mg/kg; 1 μmol) of BMB and Oxazine derivatives in 250 g SD rats 4 h prior to imaging (FIGS. 7 and 8). To compare the difference between ex vivo and in vivo results, all fluorophores used in ex vivo screening were examined in vivo in the rat brachial plexus and sciatic nerve assays. Oxazine 4 showed the highest nerve-specific fluorescence signal and the lowest background (muscle and adipose tissue) fluorescence signal compared to other molecules and BMB. Although Oxazine 1 showed no nerve fluorescence by the ex vivo nerve screening assay, it did have a weak signal in the vicinity of nerve, but could also have been caused by high adipose tissue uptake. Based on these data, Oxazine 4 was chosen for further study.

Kinetics of Oxazine 4 Nerve Targeting in Small Animals

Figure 3A:
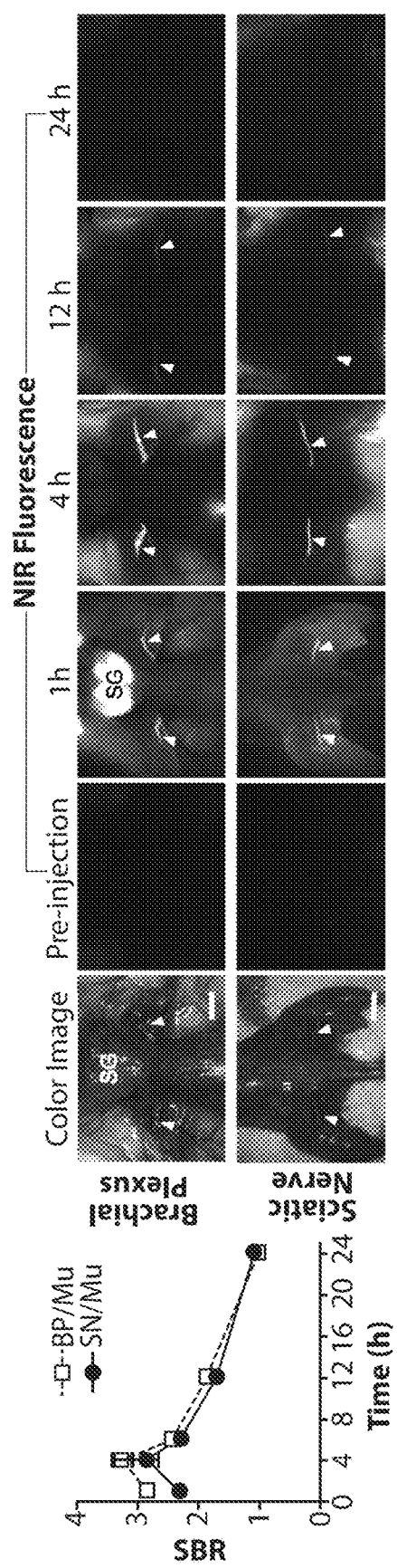
FIG. 3 shows: A) Quantitative time-course assessment of SBR (mean±SEM) for brachial plexus (BP) and sciatic nerves (SN). 100 nmol (1.6 mg/kg) of Oxazine was injected intravenously into CD-1 mice, and SBR (BP/Mu) and SBR (SN/Mu) were measured at different time points (T=0, 1, 4, 6, 12, and 24 h). Arrowheads indicate fluorescence signals in nerve bundles. SG=salivary glands; Mu=muscle. Scale bars=1 cm. All NIR fluorescence images have identical exposure times (500 msec) and normalizations. B) Dose-response curve of SBR (mean±SEM) for BP and SN. 0, 50, 100, 200, and 400 nmol of Oxazine 4 were injected intravenously into CD-1 mice, and SBR (BP/Mu) and SBR (SN/Mu) were measured at 4 h post-injection. Arrowheads indicate fluorescence signals in nerve bundles. SG=salivary glands; Mu=muscle. Scale bars=1 cm. All NIR fluorescence images have identical exposure times (500 msec) and normalizations.

The BP and SN were clearly identified and highlighted after a single intravenous injection of Oxazine 4 in CD-1 mice. In addition, small sized branches of nerves were found in the NIR image that could not be distinguished visually using color video (FIG. 3). To determine the time of peak SBR, we injected 100 nmol (1.6 mg/kg) of Oxazine 4 into mice and sacrificed N=5 per time point. The fluorescence signal in the BP and SN was bright enough by 1 h post-injection, however, the SBR was low because of high background signal from the salivary gland, adjacent muscle, adipose tissue, and skin. The highest SBR≈3.0 was achieved at 4 h post-intravenous injection, at which point surrounding background signal had decreased significantly. The background signal completely diminished after 24 h post-injection, but the fluorescence signal in nervous tissues also decayed at this time point to pre-injection levels (FIG. 3a).

Dose-Dependence of Oxazine 4 Nerve Targeting in Small Animals

Figure 3B:
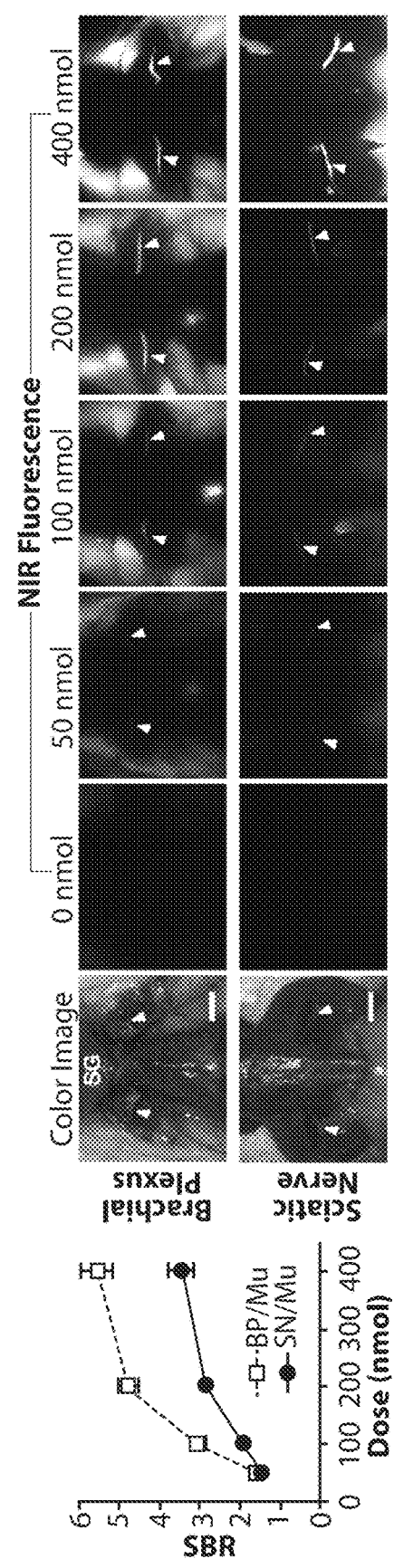

Dose-dependent optimization was investigated at 4 h post-injection. As shown in FIG. 3b, the fluorescence signals in the BP and SN were proportional to the injected dose in the range of 50-400 nmol per mouse (0.8-6.3 mg/kg). A significant difference (**$P<0.01$ for BP and *$P<0.05$ for SN) was found in the SBR between 50 nmol and 200 nmol IV injection, while there was no significant difference in the SBR of BP and SN with the dose of 200 nmol and greater ($P>0.05$) (FIG. 3b). When Oxazine 4 was injected with a 400 nmol dose, the maximal fluorescence signals were found in both BP and SN. However, the background signals in the surrounding muscle and adipose tissues were significantly increased as well. 200 nmol was therefore identified as the optimal dose.

Oxazine 4 Nerve Targeting in Large Animals

Figure 4A:
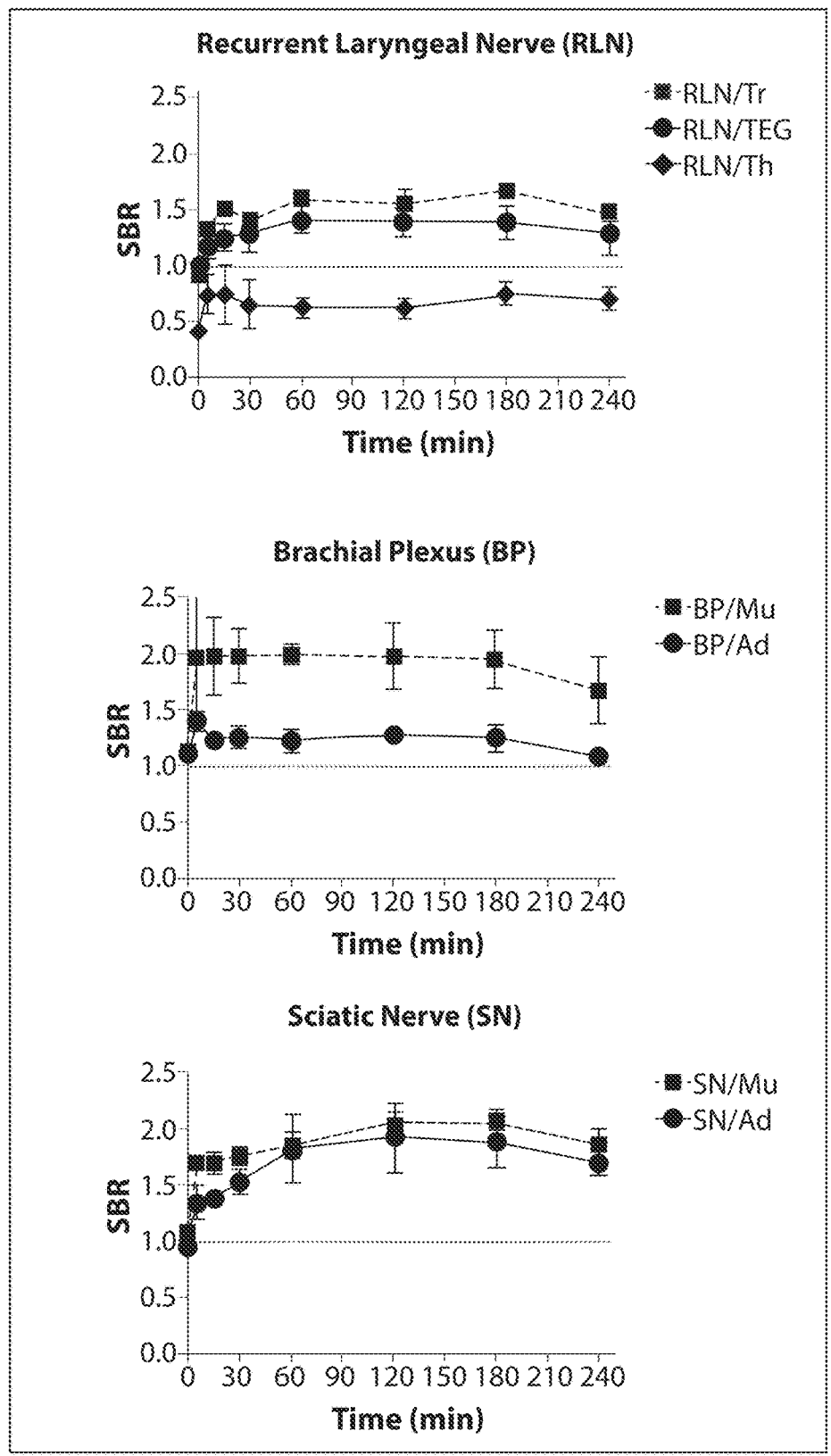
FIG. 4 shows A) Quantitative time course assessment of SBR (mean±SEM) for recurrent laryngeal nerve (RLN), brachial plexus (BP), and sciatic nerve (SN). 20 μmol (0.17 mg/kg) of Oxazine 4 was injected intravenously into 35 kg Yorkshire pigs, and the SBR of nerves to the specified surrounding tissue was measured at different time points (T=0, 15, 30, 60, 120, 180, and 240 min). B) Real-time intraoperative fluorescence images of RLN (top), BP (middle), and SN (bottom) acquired at different time points (T=0, 15, 30, 60, 120, 180, and 240 min). Ad=adipose tissue; Mu=muscle; TEG=tracheoesophageal groove; Th=thyroid; Tr=trachea. Scale bars=1 cm. Fluorescence images have identical exposure times (500 msec) and normalizations. C) Fluorescence microscopic images of cryosectioned RLN, BP, and SN. Samples were obtained after injecting 20 μmol of Oxazine 4 into Yorkshire pigs 4 h prior to resection. Shown are representative images (N=5) of H&E (left) and NIR fluorescence (right) images. Scale bars=100 m. All NIR fluorescence images have identical exposure times and normalizations.
Figure 4B:
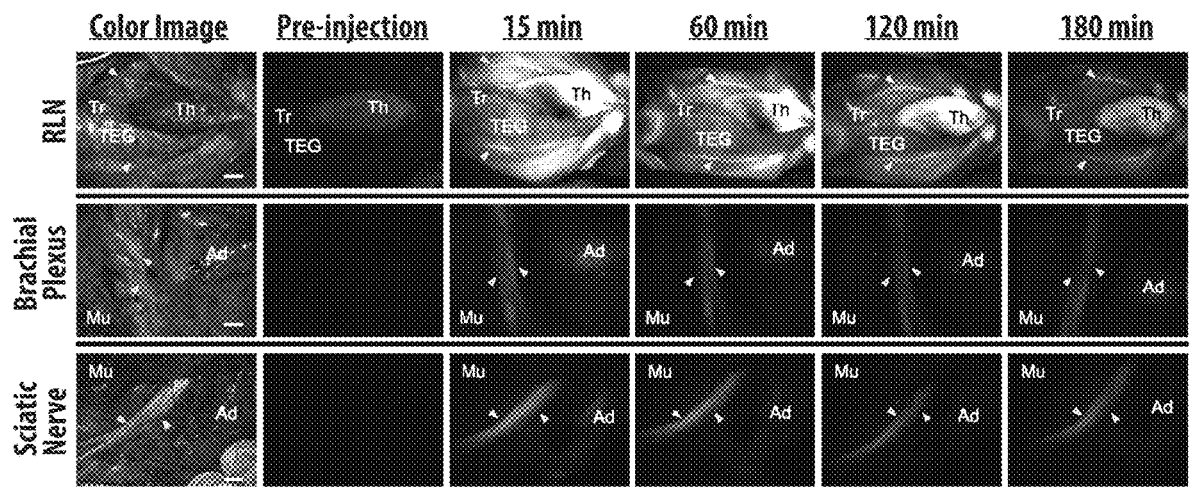

Various sites of important peripheral nerves were surgically exposed and imaged with Channel 1 (≈700 nm) of the FLARE[a] imaging system at 5, 15, 30, 60, 120, 180, and 240 min post-injection (FIG. 4). In the pre-injection images, recurrent laryngeal nerve (RLN), BP, and SN show almost no autofluorescence, however, thyroid (Th) shows relatively high autofluorescence. Since the RLN is usually located in the tracheoesophageal groove (TEG), the SBR between nerves and adjacent tissues such as trachea (Tr), TEG, and thyroid (Th) is the key determinant for preserving the RLN during surgery. The fluorescence signal in the RLN was relative high by 30 min post-injection, however, background signal in the surrounding tissue remained high at this time. The background signal decreased over time, with a maximal SBR reached at 3 h post-injection (FIG. 4a). On the other hand, BP and SN were relatively easily identified at early time points, with maximal SBR achieved at 1 h post-injection, and signal retained up to 3 h post injection (FIG. 4b).

Histological Validation of In Vivo Results

Figure 4C:
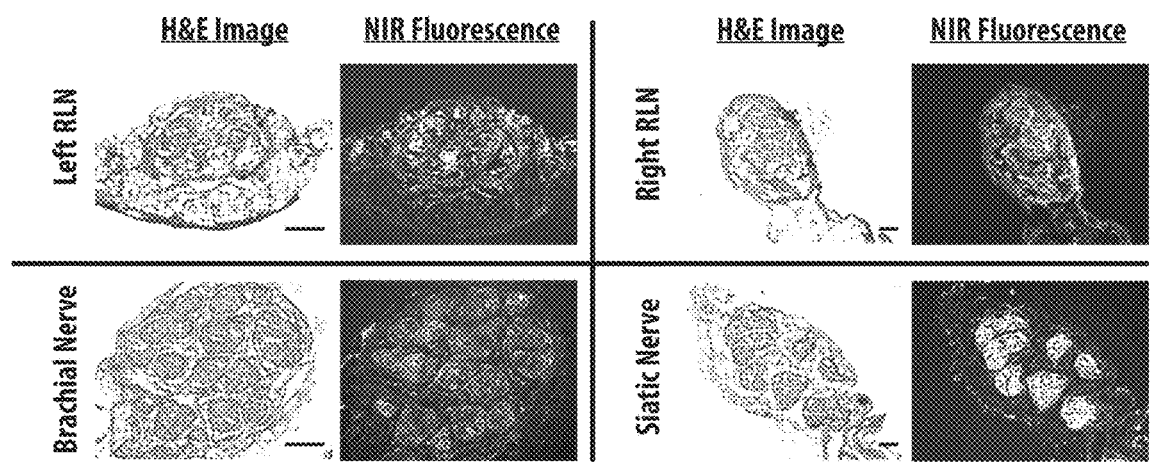
Figure 5A:
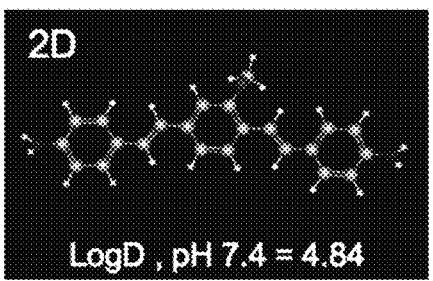
FIG. 5 shows chemical similarities between non-NIR and NIR nerve-specific contrast agents—A) BMB, and B) Oxazine 4.
Figure 5A:
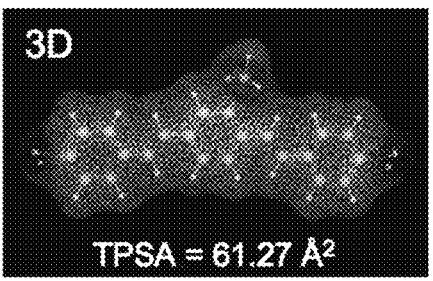
Figure 5A:
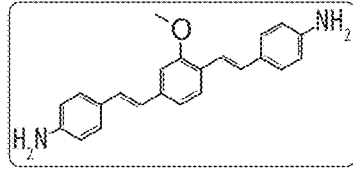
Figure 5A:
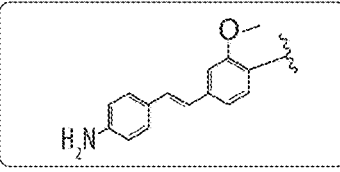
Figure 5B:
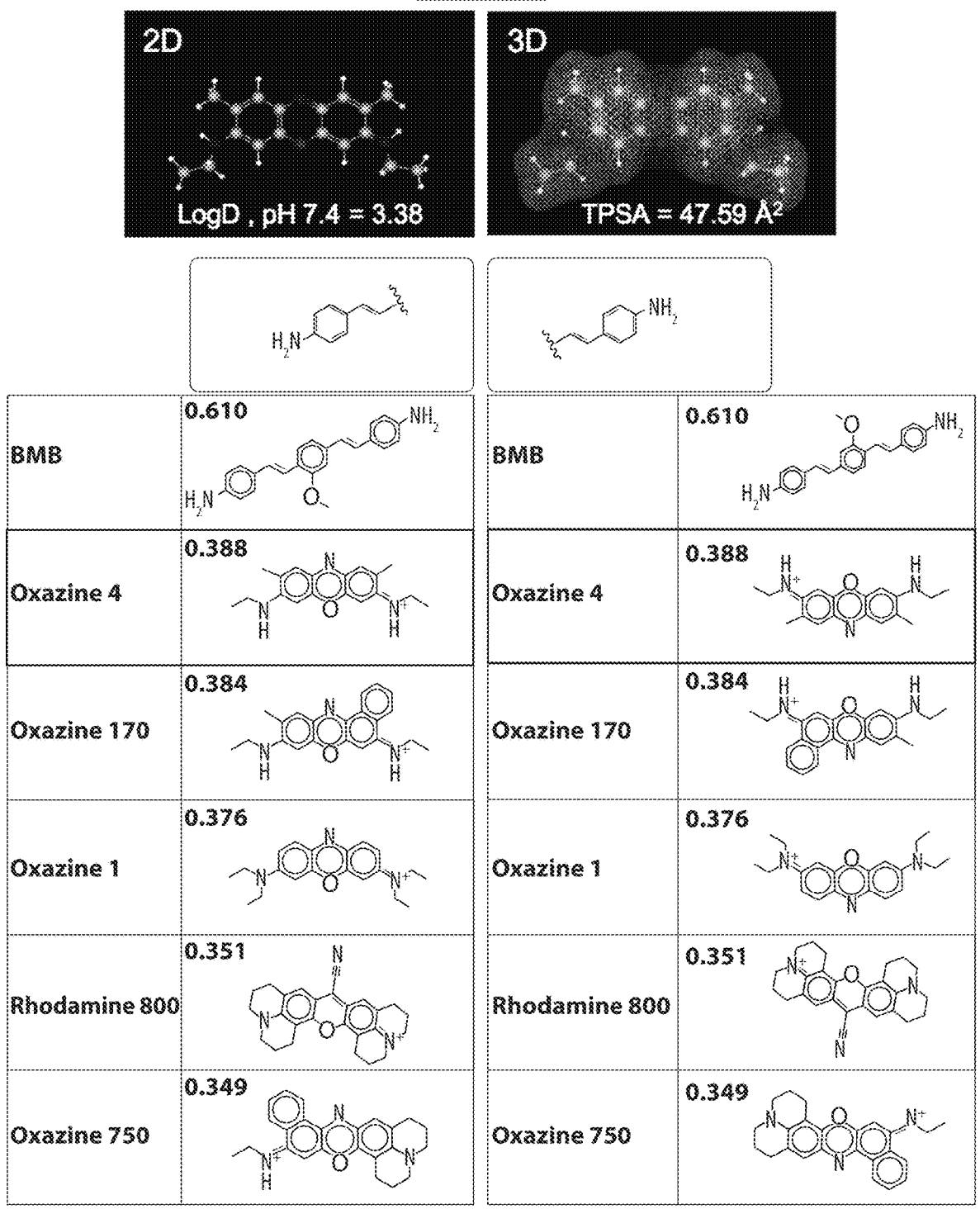

BP, SN, and RLN from pigs were resected 4 h post-injection and cryosectioned for H&E and fluorescence microscopy. As shown in FIG. 4c, NIR fluorescence microscopic images confirm bright fluorescence signal throughout the nerve cells. Fluorescence signal in the SN were higher than other nerves, consistent with the in vivo results.

Quantitative Structure-Activity Relationships (QSAR)

Figure 9:
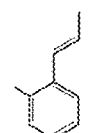
FIG. 9 shows chemical similarity of near-IR fluorophores calculated by comparing fluorophores to positive nerve binding fingerprints proposed by Gibbs et al. (PLoS One 2013; 8, e73493). Based on the QSAR screening and fingerprinting, Oxazine 4 fits with the previously proposed basic requirement of a balanced para-configuration of the core. In addition, Oxazine 4 shows the highest similarity with the five highest ranked fingerprints except for BMB. Although Oxazine 170 and Rhodamine 800 show relatively high similarities, the former is rather lipophilic (logD at pH 7.4=3.94) and the latter is rather hydrophilic (logD at pH 7.4=0.43), which resulted in high accumulation in adipose tissue or low targeting affinity to the nerve, respectively.

Based on the QSAR screening and chemical group fingerprinting of BMB (13), we compared the five positive fingerprints with our new nerve-targeting fluorophores. Among the series, Oxazine 4 met the basic requirement of a balanced para configuration of the core (FIG. 9; (13)). In addition, Oxazine 4 showed the highest similarity with the five highest ranked fingerprints except for BMB (FIG. 9). When compared to the chemical structure of BMB and its constituent groups (FIG. 5), Oxazine 4 also ranked top in most cases. Rhodamine 800 scored higher for some fragments, but its uptake in nerve was low because of its low log D at pH 7.4 (0.43). Conversely, Oxazine 170 and Oxazine 750, which have high log D at pH 7.4 values (3.94 and 4.67, respectively) showed strong adipose uptake both ex vivo and in vivo.

DISCUSSION

The criteria for an ideal nerve cell-specific contrast agent for image-guided surgery include a log D at pH 7.4 between 0.5 to 3 and a molecular weight <500 Da to maximize blood-nerve-barrier (BNB) penetration, excitation and emission wavelengths in the NIR window, and prolonged retention (22). To the best of our knowledge, Oxazine 4 is the first small molecule described to date that meets all criteria. Based on its chemical similarity to BMB, without wishing to be bound by theory, Oxazine 4 likely targets myelin or a closely associated molecule.

Improvements to the properties of Oxazine 4 are contemplated. First, in Oxazine 4, peak excitation and emission are below rather than above 700 nm. In an ideal molecule, both properties should be near 800 nm or above. Our chemical structure analysis, though, suggests how to improve optical properties. Closure of the right quaternary amine into a ringed structure should cause a bathochromic shift of the resonant structure. It would be desirable to add these additional double bonds while maintaining a log D at pH 7.4 that is compatible with crossing the BNB. Second, it is known from previous studies (13) that certain chemical groups appear to increase undesired uptake in adipose tissue. Comparison of structures from Oxazine 1 (high adipose, low nerve signal) to Oxazine 4 (moderate adipose, high nerve signal) helps one avoid this problem. Third, the log D at pH 7.4, which previous work in the field has suggested should be between 0.5 and 3 (23, 24), may desirably be lower than in Oxazine 4. And, finally, all three of these optimizations preferably do not increase molecular weight higher than 500 Da, because above this value BNB penetration falls off drastically (23, 24).

In vivo biodistribution and clearance mediate how long after intravenous injection a contrast agent reaches peak SBR, and how long the signal lasts. The pharmacokinetic data presented in FIGS. 3A and 4 suggest that nerve penetration is rapid, blood and tissue clearance is rapid, yet retention in nerves is strong enough to permit an SBR>1 for many hours. After performing the optical and chemical properties optimization described above, attention will need to be turned to nerve affinity. Increasing affinity will further improve nerve retention while also increasing signal strength and the imaging period.

It should be noted that the optimal dose of the molecules we describe in this study is 10-50 fold lower than previously described nerve-specific fluorophores and corresponds to a human-equivalent dose of only 0.2 mg/kg, which is consistent with the clinically-approved dose of the NIR fluorophore indocyanine green (ICG).

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

1. A. J. Cohen et al., Phrenic nerve injury after coronary artery grafting: is it always benign? *Ann Thorac Surg* 64, 148 (July, 1997).
2. I. A. Chaudhary, Samiullah, R. Masood, M. A. Majrooh, A. A. Mallhi, Recurrent laryngeal nerve injury: an experience with 310 thyroidectomies. *J Ayub Med Coll Abbottabad* 19, 46 (July-September, 2007).
3. R. W. Clough et al., Cortical edema in moderate fluid percussion brain injury is attenuated by vagus nerve stimulation. *Neuroscience* 147, 286 (Jun. 29, 2007).
4. C. Shi, S. R. Flanagan, U. Samadani, Vagus nerve stimulation to augment recovery from severe traumatic brain injury impeding consciousness: a prospective pilot clinical trial. *Neurol Res* 35, 263 (April, 2013).
5. B. H. Lang, C. Y. Lo, W. F. Chan, K. Y. Lam, K. Y. Wan, Staging systems for papillary thyroid carcinoma: a review and comparison. *Ann Surg* 245, 366 (March, 2007).
6. S. K. Snyder, T. C. Lairmore, J. C. Hendricks, J. W. Roberts, Elucidating mechanisms of recurrent laryngeal nerve injury during thyroidectomy and parathyroidectomy. *J Am Coll Surg* 206, 123 (January, 2008).
7. D. Myssiorek, Recurrent laryngeal nerve paralysis: anatomy and etiology. *Otolaryngol Clin North Am* 37, 25 (February, 2004).
8. C. Wu et al., Molecular probes for imaging myelinated white matter in CNS. *J Med Chem* 51, 6682 (Nov. 13, 2008).
9. C. Wu et al., A novel fluorescent probe that is brain permeable and selectively binds to myelin. *J Histochem Cytochem* 54, 997 (September, 2006).
10. B. Stankoff et al., Imaging of CNS myelin by positron-emission tomography. *Proc Natl Acad Sci USA* 103, 9304 (Jun. 13, 2006).
11. J. R. Meyers et al., Lighting up the senses: FM1-43 loading of sensory cells through nonselective ion channels. *J Neurosci* 23, 4054 (May 15, 2003).
12. S. L. Gibbs-Strauss et al., Molecular imaging agents specific for the annulus fibrosus of the intervertebral disk. *Mol Imaging* 9, 128 (June, 2010).
13. S. L. Gibbs et al., Structure-activity relationship of nerve-highlighting fluorophores. *PLoS One* 8, e73493 (2013).
14. V. E. Cotero et al., Intraoperative fluorescence imaging of peripheral and central nerves through a myelin-selective contrast agent. *Mol Imaging Biol* 14, 708 (December, 2012).
15. A. Nakayama, A. C. Bianco, C. Y. Zhang, B. B. Lowell, J. V. Frangioni, Quantitation of brown adipose tissue perfusion in transgenic mice using near-infrared fluorescence imaging. *Mol Imaging* 2, 37 (January, 2003).
16. M. A. Whitney et al., Fluorescent peptides highlight peripheral nerves during surgery in mice. *Nat Biotechnol* 29, 352 (April, 2011).
17. A. P. Wu et al., Improved facial nerve identification with novel fluorescently labeled probe. *The Laryngoscope* 121, 805 (April, 2011).
18. H. S. Choi et al., Targeted zwitterionic near-infrared fluorophores for improved optical imaging. *Nat Biotechnol* 31, 148 (February, 2013).
19. Y. Ashitate et al., Two-wavelength near-infrared fluorescence for the quantitation of drug antiplatelet effects in large animal model systems. *J Vasc Surg* 56, 171 (July, 2012).
20. H. S. Choi et al., Rapid translocation of nanoparticles from the lung airspaces to the body. *Nat Biotechnol* 28, 1300 (December, 2010).
21. B. Trojanowicz et al., Retinoic acid-mediated down-regulation of ENO1/MBP-1 gene products caused decreased invasiveness of the follicular thyroid carcinoma cell lines. *J Mol Endocrinol* 42, 249 (March, 2009).
22. H. Pajouhesh, G. R. Lenz, Medicinal chemical properties of successful central nervous system drugs. *NeuroRx* 2, 541 (October, 2005).
23. U. Fagerholm, The highly permeable blood-brain barrier: an evaluation of current opinions about brain uptake capacity. *Drug Discov Today* 12, 1076 (December, 2007).
24. R. N. Waterhouse, Determination of lipophilicity and its use as a predictor of blood-brain barrier penetration of molecular imaging agents. *Mol Imaging Biol* 5, 376 (November-December, 2003).
25. S. L. Gibbs-Strauss et al., Nerve-highlighting fluorescent contrast agents for image-guided surgery. *Mol Imaging* 10, 91 (April, 2011).
26. S. L. Troyan et al., The FLARE intraoperative near-infrared fluorescence imaging system: a first-in-human clinical trial in breast cancer sentinel lymph node mapping. *Ann Surg Oncol* 16, 2943 (October, 2009).
27. S. Gioux et al., High-power, computer-controlled, light-emitting diode-based light sources for fluorescence imaging and image-guided surgery. *Mol Imaging* 8, 156 (May-June, 2009).
28. Y. Ashitate, A. Stockdale, H. S. Choi, R. G. Laurence, J. V. Frangioni, Real-time simultaneous near-infrared fluorescence imaging of bile duct and arterial anatomy. *J Surg Res* 176, 7 (July, 2012).
29. K. W. Kelley, S. E. Curtis, G. T. Marzan, H. M. Karara, C. R. Anderson, Body surface area of female swine. *J Anim Sci* 36, 927 (May, 1973).
30. S. Reagan-Shaw, M. Nihal, N. Ahmad, Dose translation from animal to human studies revisited. *Faseb J* 22, 659 (March, 2008).

The contents of all patent, patent applications, and publications cited herein are incorporated herein by reference in their entireties.

What is claimed is:
1. A method of imaging tissue or cells, the method comprising:
 (a) intravenously administering an imaging composition to an organism comprising the tissue or cells, wherein the imaging composition consists essentially of an imaging agent and wherein the intravenous administering comprises contacting the tissue or cells with the imaging agent, wherein the imaging agent is Oxazine 4 perchlorate (OX4);
 (b) irradiating the tissue or cells contacted with the imaging agent at a wavelength absorbed by the imaging agent to provide irradiated tissue or cells; and
 (c) detecting an optical signal from the irradiated tissue or cells, thereby imaging the tissue or cells, wherein the imaging agent is selectively absorbed by nerve tissue or nerve cells and the selectivity is at least 2:1 relative to muscle cells.

2. The method of claim 1, wherein the tissue or cells is nerve tissue or nerve cells.

3. The method of claim 1, wherein the organism is human.

4. The method of claim 1, wherein the imaging agent has peak absorbance at about 600 nm to 850 nm.

5. The method of claim 1, wherein the tissue or cells is imaged ex vivo.

* * * * *

UNITED STATES PATENT AND TRADEMARK OFFICE
CERTIFICATE OF CORRECTION

Page 1 of 1

PATENT NO. : 11,001,562 B2
APPLICATION NO. : 15/033322
DATED : May 11, 2021
INVENTOR(S) : Frangioni et al.

It is certified that error appears in the above-identified patent and that said Letters Patent is hereby corrected as shown below:

In the Specification

At Column 1, Lines 17-19:
Delete:
"This invention was made with government support under CA115296, EB010022, and EB011523 awarded by NIH. The Government has certain rights in the invention."

Insert:
--This invention was made with government support under grant numbers CA115296, EB010022, and EB011523 awarded by the National Institutes of Health. The Government has certain rights in the invention.--

Signed and Sealed this
Tenth Day of February, 2026

John A. Squires
*Director of the United States Patent and Trademark Office*